US008790653B2

(12) United States Patent
Herkel et al.

(10) Patent No.: US 8,790,653 B2
(45) Date of Patent: Jul. 29, 2014

(54) PEPTIDE INHIBITORS FOR MEDIATING STRESS RESPONSES

(75) Inventors: Johannes Herkel, Hamburg (DE); Irun R. Cohen, Rehovot, IL (US); Varda Rotter, Rishon le Zion (IL); Ansgar W. Lohse, Mainz (DE); Neta Erez, Tel-Aviv (IL); Avishai Mimran, Rehovot (IL); Na'aman Kam, Givataim (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/287,098

(22) Filed: Nov. 1, 2011

(65) Prior Publication Data

US 2012/0171233 A1 Jul. 5, 2012

Related U.S. Application Data

(62) Division of application No. 11/573,707, filed as application No. PCT/IL2005/000908 on Aug. 23, 2005, now Pat. No. 8,067,008.

(60) Provisional application No. 60/603,255, filed on Aug. 23, 2004.

(51) Int. Cl.
| A61K 39/00 | (2006.01) |
| A61K 38/00 | (2006.01) |
| A61K 38/08 | (2006.01) |
| A61K 38/10 | (2006.01) |
| A61K 38/16 | (2006.01) |
| C07K 16/18 | (2006.01) |
| C07K 7/00 | (2006.01) |
| C07K 7/06 | (2006.01) |
| C07K 7/08 | (2006.01) |
| C07K 14/00 | (2006.01) |

(52) U.S. Cl.
USPC ....... 424/185.1; 514/1.1; 514/21.3; 514/21.4; 514/21.5; 514/21.6; 514/21.7

(58) Field of Classification Search
None
See application file for complete search history.

(56) References Cited

U.S. PATENT DOCUMENTS

| 4,946,778 A | 8/1990 | Ladner |
| 5,091,513 A | 2/1992 | Huston |
| 5,096,815 A | 3/1992 | Ladner |
| 5,223,409 A | 6/1993 | Ladner et al. |
| 5,338,665 A | 8/1994 | Schatz et al. |
| 5,432,018 A | 7/1995 | Dower et al. |
| 5,498,530 A | 3/1996 | Schatz et al. |
| 5,733,731 A | 3/1998 | Schatz et al. |
| 5,910,573 A | 6/1999 | Pluckthun |
| 5,922,545 A | 7/1999 | Mattheakis et al. |
| 6,294,353 B1 | 9/2001 | Pack |
| 6,420,136 B1 | 7/2002 | Riabowol et al. |
| 6,593,353 B1 | 7/2003 | Gudkov et al. |
| 6,630,584 B1 | 10/2003 | Solomon et al. |
| 6,723,567 B1 | 4/2004 | Harr et al. |
| 6,726,895 B2 | 4/2004 | Strauss et al. |
| 7,030,090 B2 | 4/2006 | Ryu et al. |
| 7,517,857 B2 | 4/2009 | Ryu et al. |
| 7,622,455 B2 | 11/2009 | Bennett et al. |
| 7,659,243 B2 | 2/2010 | Greenway et al. |
| 2005/0281816 A1 | 12/2005 | Lamping |
| 2006/0014719 A1 | 1/2006 | Chang |
| 2008/0045456 A1 | 2/2008 | Greenway et al. |
| 2008/0267983 A1 | 10/2008 | Herkel et al. |
| 2009/0169649 A1 | 7/2009 | Hovens et al. |
| 2009/0324549 A1 | 12/2009 | Battaglia et al. |
| 2010/0009364 A1 | 1/2010 | Fantl et al. |
| 2010/0099700 A1 | 4/2010 | Hung |
| 2010/0292281 A1 | 11/2010 | Lovell et al. |
| 2010/0298306 A1 | 11/2010 | Herbert et al. |
| 2014/0088017 A1 | 3/2014 | Ovadia et al. |

FOREIGN PATENT DOCUMENTS

| CN | 1692126 | 11/2005 |
| EP | 1408114 | 4/2004 |
| JP | 2006-505503 | 2/2006 |
| WO | WO 94/12202 | 6/1994 |
| WO | WO 96/37621 | 11/1996 |
| WO | WO 96/40987 | 12/1996 |
| WO | WO 98/15833 | 4/1998 |
| WO | WO 98/52558 | 11/1998 |
| WO | WO 98/56416 | 12/1998 |
| WO | WO 99/23091 | 5/1999 |
| WO | WO 99/32463 | 7/1999 |
| WO | WO 00/23082 | 4/2000 |
| WO | WO 01/01986 | 1/2001 |
| WO | WO 03/099868 | 12/2003 |
| WO | WO 2004/035793 | 4/2004 |
| WO | WO 2006/021954 | 3/2006 |
| WO | WO 2011/017030 | 2/2011 |
| WO | WO 2012/160563 | 11/2012 |

OTHER PUBLICATIONS

Bruijn et al (Ann. Rev. Neurosci., 2004, 27: 723-749).*
Rudikoff et al (Proc Natl Acad Sci USA 1982 vol. 79 p. 1979).*
Casset et al (2003 BBRC 307, 198-205).*
Mayo Clinic, Infertility—Causes, mayoclinic.com/health/infertility/DS00310/DSECTION=causes, 2013.*
Zheng et al (Diabetes, 2005, 54: 1423-1428).*
Translation of Decision of Rejection Dated Dec. 5, 2012 From the State Intellectual Property Office of the People's Republic of China Re. Application No. 200580028458.7.
Office Action Dated Jul. 28, 2009 From the Israel Patent Office Re. Application No. 1281471 and Its Translation Into English.

(Continued)

*Primary Examiner* — Gerald R Ewoldt
*Assistant Examiner* — Marianne DiBrino

(57) ABSTRACT

The present invention relates to peptides capable of inhibiting cellular and immune stress responses in a eukaryotic cell. The invention provides compositions and methods for the treatment of human degenerative diseases and inflammation, utilizing these peptides.

4 Claims, 8 Drawing Sheets

(56) References Cited

OTHER PUBLICATIONS

Communication Pursuant to Article 94(3) EPC Dated Feb. 11, 2013 From the European Patent Office Re. Application No. 05774723.0.
Office Action Dated Feb. 5, 2013 From the Israel Patent Office Re. Application No. 1281471 and Its Translation Into English.
European Search Report and the European Search Opinion Dated Mar. 11, 2013 From the European Patent Office Re. Application No. 11181049.5.
Requisition by the Examiner Dated May 10, 2013 From the Canadian Intellectual Property Office Re. Application No. 2,577,196.
Translation of Office Action Dated Apr. 27, 2012 From the State Intellectual Property Office of the People's Republic of China Re. Application No. 200580028458.7.
Dewil et al. "Vascular Endothelial Growth Factor Counteracts the Loss of Phospho-Akt Preceding Motor Neurone Degeneration in Amyotrophic Lateral Sclerosis", Neuropathology and Applied Neurobiology, 33: 499-509, 2007.
Léger et al. "Human Skeletal Muscle Atrophy in Amyotrophic Lateral Sclerosis Reveals A Reduction in Akt and an Increase in Atrogin-1", The FASEB Journal, 20(3): 583-585, Jan. 17, 2006.
Examination Report Dated Jul. 17, 2012 From the Government of India, Patent Office, Intellectual Property Building Re. Application No. 1729/DELNP/2007.
International Search Report and the Written Opinion Dated Oct. 9, 2012 From the International Searching Authority Re.: Application No. PCT/IL2012/050185.
Baker S.J. et al., "Suppression of human colorectal carcinoma cell growth by wild-type p53," *Science*, 249(4971):912-915 (Aug. 24, 1990).
Cohen I.R., "Discrimination and dialogue in the immune system," *Semin Immunol*,12(3):215-219 (Jun. 2000).
Crameri et al., "A-Geneseq_8 Accession No. ADM57310," Jul. 1, 2004.
Cwirla S.E. et al., "Peptide agonist of the thrombopoietin receptor as potent as the natural cytokine," *Science*, 276(5319):1696-1699 (Jun. 13, 1997).
Dedman J.R. et al., "Selection of targeted biological modifiers from a bacteriophage library of random peptides. The identification of novel calmodulin regulatory peptides," *J Biol Chem.*, 268(31):23025-23030 (Nov. 5, 1993).
Devlin J.J. et al., "Random peptide libraries: a source of specific protein binding molecules," *Science*, 249(4967):404-406 (Jul. 27, 1990).
Dinarello C.A., "Interleukin-1," *Rev Infect Dis*, 6(1):51-95 (Jan.-Feb. 1984).
el-Deiry W.S. et al., "Definition of a consensus binding site for p53," *Nat Genet.*, 1(1):45-49 (Apr. 1992).
Ellis R.E. et al., "Mechanisms and functions of cell death," *Annu Rev Cell Biol.*, 7:663-698 (1991).
Ershler W.B. et al., "Immunologic aspects of osteoporosis," *Dev Comp Immunol*, 21(6):487-499 (Nov.-Dec. 1997).
Foord O.S. et al., "A DNA binding domain is contained in the C-terminus of wild type p53 protein," *Nucleic Acids Res.*, 19(19):5191-5198 (Oct. 11, 1991).
Gavrieli Y. et al., "Identification of programmed cell death in situ via specific labeling of nuclear DNA fragmentation," *J Cell Biol*, 119(3):493-501 (Nov. 1992).
Gruol D.L. et al., "Physiological and pathological roles of interleukin-6 in the central nervous system," *Mol Neurobiol*, 15(3):307-339 (Dec. 1997).
Haunstetter A. et al., "Apoptosis: basic mechanisms and implications for cardiovascular disease," *Circ Res.*, 82(11):1111-1129 (Jun. 15, 1998).
Herkel J. et al., "Systemic lupus erythematosus in mice, spontaneous and induced, is associated with autoimmunity to the C-terminal domain of p53 that recognizes damaged DNA," *Eur J Immunol.*, 30(4):977-984 (Apr. 2000).
Herkel J. et al., "Monoclonal antibody to a DNA-binding domain of p53 mimics charge structure of DNA: anti-idiotypes to the anti-p53 antibody are anti-DNA," *Eur J Immunol*, 34(12):3623-3632 (Dec. 2004).

Hollstein M. et al., "p53 mutations in human cancers," *Science*, 253(5015):49-53 (Jul. 5, 1991).
Kastan M.B. et al., "Participation of p53 protein in the cellular response to DNA damage," *Cancer Res.*, 51(23 Pt 1):6304-6311 (Dec. 1, 1991).
Kay et al., Drug Disc. Today 3: 370-378 (1998).
Ko L.J. et al., "p53: puzzle and paradigm," *Genes Dev.*, 10(9):1054-1072 (May 1, 1996).
Komarova E.A. et al., "Chemoprotection from p53-dependent apoptosis: potential clinical applications of the p53 inhibitors," *Biochem Pharmacal.*, 62(6):657-67 (May 1, 1996).
Kuerbitz S.J. et al., "Wild-type p53 is a cell cycle checkpoint determinant following irradiation," *Proc Natl Acad Sci U S A*, 89(16):7491-7495 (Aug. 15, 1992).
Lee, K. H. et al., "Peptide recognition by an anti-idiotypic antibody against angiotensin II: Peptide library search for peptides other than angiotensin II," *Biophysical Jour.* 68(2 part 2):A406 (1995).
Lee S. et al., "p53 and its 14 kDa C-terminal domain recognize primary DNA damage in the form of insertion/deletion mismatches," *Cell*,81(7):1013-1020 (Jun. 30, 1995).
Liu, G. Y. et al., "Low avidity recognition of self-antigen by T cells permits escape from central tolerance," *Immunity*, 3:407-415 (1995).
Lomas, M. et al., "Phase I clinical trial of a human idiotypic p53 vaccine in patients with advanced malignancy," *Annals of Oncology*, 15(2):324-329 (2004).
Lowman H.B. et al., "Bacteriophage display and discovery of peptide leads for drug development," *Annu Rev Biophys Biomol Struct.*, 26:401-424 (1997).
Mattson M.P. et al., "Neurodegenerative disorders and ischemic brain diseases," *Apoptosis*, 6(12):69-81 (Feb.-Apr. 2001).
Martin L.J., "Neuronal cell death in nervous system development, disease, and injury," *Int J Mol Med.*, 7(5):455-478 (May 2001).
Nathan C., "Points of control in inflammation," *Nature*, 420(6917):846-852 (Dec. 19-26, 2002).
Nickells R.W., "Apoptosis of retinal ganglion cells in glaucoma: an update of the molecular pathways involved in cell death," *Surv Ophthalmol.*, 43 Suppl 1:S151-S161 (Jun. 1999).
Nicoletti I. et al., "A rapid and simple method for measuring thymocyte apoptosis by propidium iodide staining and flow cytometry," *J Immunol Methods*, 139(2):271-279 (Jun. 3, 1991).
Nitta M. et al., "Heat shock induces transient p53-dependent cell cycle arrest at G1/S," *Oncogene*, 15(5):561-568 (Jul. 31, 1997).
Pisetsky D,S., "The immunologic properties of DNA," *J Immunol.*, 156(2):421-423 (Jan. 15, 1996).
Radic M.Z. et al., "Genetic and structural evidence for antigen selection of anti-DNA antibodies," *Annu Rev Immunol.*, 12:487-520 (1994).
Raghupathi R. et al., "Apoptosis after traumatic brain injury," *J Neurotrauma*.17(10):927-938 (Oct. 2000).
Rankin E.C. et al., "The therapeutic effects of an engineered human anti-tumour necrosis factor alpha antibody (CDP571) in rheumatoid arthritis," *Br J Rheumatol*, 34(4):334-342 (Apr. 1995).
Roberts R.W. et al., "RNA-peptide fusions for the in vitro selection of peptides and proteins," *Proc Natl Acad Sci U S A.*, 94(23):12297-12302 (Nov. 11, 1997).
Scott J.K. et al., "Searching for peptide ligands with an epitope library," *Science*, 249(4967)386-391 (Jul. 27, 1990).
Shohami E. et al., "Cytokine production in the brain following closed head injury: dexanabinol (HU 211) is a novel TNF-alpha inhibitor and an effective neuroprotectant," *J Neuroimmunol*, 72(2):169-177 (Feb. 1997).
Stack W.A. et al., "Randomised controlled trial of CDP571 antibody to tumour necrosis factor-alpha in Crohn's disease," *Lancet*, 349(9051):521-524 (Feb. 22, 1997).
Takasaki W. et al., "Structure-based design and characterization of exocyclic peptidomimetics that inhibit TNF alpha binding to its receptor," *Nat Biotechnol*, 15(12):1266-1270 (Nov. 1997).
Thompson C.B. et al., "Apoptosis in the pathogenesis and treatment of disease," *Science*, 267(5203):1456-1462 (Mar. 10, 1995).
Treon S.P. et al., "Interleukin-6 in multiple myeloma and related plasma cell dyscrasias," *Curr Opin Hematol*, 5(1):42-48 (Jan. 1998).
Van Regenmortel M.H. et al., "D-peptides as immunogens and diagnostic reagents," *Curr Opin Biotechnol*,9(4):377-382 (Aug. 1998).

(56) References Cited

OTHER PUBLICATIONS

Wang, X. et al., "Tumor associated antigen (TAA) mimicry and immunotherapy of malignant diseases from anti-idiotypic antibodies to peptide mimics," *Cancer Chemo. & Biolog. Resp. Modifiers*, 19:309-326 (2001).
Wells J.A. et al., "Rapid evolution of peptide and protein binding properties in vitro," *Curr Opin Biotechnol.*, 3(4):355-362 (Aug. 1992).
Wilson D.R. et al., "Phage display: applications, innovations, and issues in phage and host biology," *Can J Microbiol*, 44(4):313-329 (Apr. 1998).
Wolf D. et al., "Reconstitution of p53 expression in a nonproducer Ab-MuLV-transformed cell line by transfection of a functional p53 gene," *Cell*, 38(1):119-126 (Aug. 1984).
Yonish-Rouach E. et al., "Wild-type p53 induces apoptosis of myeloid leukaemic cells that is inhibited by interleukin-6," *Nature*, 352(6333):345-347 (Jul. 25, 1991).
International Search Report and Written Opinion dated Nov. 7, 2006 from the International Searching Authority re application No. PCT/IL2005/000908.
International Preliminary Report on Patentability dated Feb. 28, 2007 from the IB of WIPO re application No. PCT/IL2005/000908.
Notification of European Publication Number and Information on the Application of Article 67(3) EPC dated Apr. 12, 2007 from the European Patent Office re application No. 05774723.0.
Supplementary European Search Report and European Search Opinion dated Jun. 23, 2009 from the European Patent Office re application No. 95774723.0.
Proceedings Further with the European Patent Application Pursuant to Rule 70(2) EPC dated Jul. 10, 2009 from the European Patent Office re application No. 05774723.0.
Response dated Dec. 24, 2009 to Office Action of Jul. 23, 2009 from the Israel Patent Office re application No. 1281471.
Communication Pursuant to Article 94(3) EPC dated Sep. 4, 2009 from the European Patent Office re application No. 05774723.0.
Response dated Jan. 27, 2010 to Communication Pursuant to Article 94(3) EPC dated Sep. 4, 2009 from the European Patent Office re application No. 05774723.0.
Translation of Official Action dated Nov. 16, 2010 from the Japanese Patent Office re application No. 2007-529133.
Response dated Dec. 2, 2010 to Office Action of Aug. 4, 2010 from the Israel Patent Office re application No. 1281471.
Response dated Feb. 8, 2011 to Official Action dated Nov. 16, 2010 from the Japanese Patent Office re application No. 2007-529133.
Noting of Loss of Rights Pursuant to Rule 112(1) EPPC dated Apr. 4, 2011 from the European Patent Office re application No. 05774723.0.
Translation of Office Action dated Jul. 6, 2011 fro the State Intellectual Property Office of the People's Republic of China re application No. 200580028458.7.
Translation of Official Action dated Jul. 8, 2011 from the Japanese Patent Office re application No. 2007-529133.
Examiner's Report dated Aug. 16, 2011 from the Australian Government, IP Australia, re ppplication No. 2005276117.
Notice of Allowance dated Jul. 15, 2011 from the USPTO re U.S. Appl. No. 11/573,707.
Office Action dated Aug. 4, 2010 from the Israel Patent Office re Application No. 1281471.
Office Action dated Feb. 9, 2009 from the Israel Patent Office re Application No. 1281471.
Office Action dated Jul. 28, 2009 from the Israel Patent Office re Application No. 1281471.
Office Action dated Oct. 7, 2010 from the USPTO re U.S. Appl. No. 11/573,707.
Office Action dated Feb. 10, 2011 from the USPTO re U.S. Appl. No. 11/573,707.
Response dated Nov. 3, 3011 to Official Action of Jul. 8, 2011 from the Japanese Patent Office re Application No. 2007-529133.
Requisition by the Examiner Dated May 24, 2012 From the Canadian Intellectual Property Office Re. Application No. 2,577,196.
Hearing Notice Dated Jan. 17, 2014 From the Government of India, Patent Office, Intellectual Property Building Re. Application No. 1729/DELNP/2007.
International Preliminary Report on Patentability Dated Apr. 3, 2014 From the International Bureau of WIPO Re. Application No. PCT/IL2012/050185.
Office Action Dated Feb. 14, 2014 From The State Intellectual Property Office of the People's Republic of China Re. Application No. 201310079356.4 and Its Translation Into English.
Search Report Dated Feb. 14, 2014 From The State Intellectual Property Office of the People's Republic of China Re. Application No. 201310079356.4 and Its Translation Into English.

* cited by examiner

A)

|  | CDR 1 | CDR 2 |
|---|---|---|
| PAb-421_VL | DIQLTQSPLTLSVTIGQPASISCKSSQSLLDSDGKTYLNWLLQRPGQSPKRLIYLVSKLDS |
| Idi-1_VL | DIVITQDELSNPVTSGESVSISCR..QSLLYKNGKTYLNWFLQRPGQSPQLLIYLMSIRAS |
| Idi-2_VL | NIVMTQSPASLAVSLGQRATISCQASESVSF.AGTSLMHWYQQKPGQPPKLLIYRASKLES |

|  | CDR 3 |
|---|---|
| PAb-421_VL | GVPDRFTGSGSGTDFTLKINRVEAEDLGVYYCWQGTHSPLTFGAGTKL |
| Idi-1_VL | GVSDRFSGNGSGTDFTLEISRVRAEDVGVYYCQQLVEYPYTFGGGTKL |
| Idi-2_VL | GVPARFSGSGSESDFTLTIDPVEEDDAAMYYCMQSMEDPYTFGGGTKL |

B)

|  | CDR 1 | CDR 2 |
|---|---|---|
| PAb-421_VH | QVKLQESGAELVRSGASVKLSCTASGFNITDYYMHWVKQRPEQGLEWIGWIDPENG DTEYA |
| Idi-1_VH | QVQLQQSGAELVRPGASVKLSCKASGYIFTSYWINWVRQRPGQGLEWIGNISPADSSTNYN |
| Idi-2_VH | QVQLQQSGPELVKPGASMKISCKASGYSFTGYTINWVKQSHGKNLEWIGLINPYNGGTCYN |

|  | CDR 3 |
|---|---|
| PAb-421_VH | QKFKGKATMTADTSSNTAYLQLSSLTSEDTAVYYCNFYGDAL........DYWGQGTTVTVSS |
| Idi-1_VH | QKFKDKATLTVDKSSTTAYMQLSRPTFEDSAVYYCAREEVRRRDM....DFWGQGTSV |
| Idi-2_VH | PKFKGKATLTVDKSSSTAYMELLSLTSEDSAVYYCARRVWLRRDGFYYAMDYWGQGTSV |

Figure 7

PEPTIDE INHIBITORS FOR MEDIATING STRESS RESPONSES

RELATED APPLICATION DATA

This application is a divisional of U.S. patent application Ser. No. 11/573,707 filed on Apr. 16, 2008 now U.S. Pat. No. 8,067,008, which is the U.S. national stage of PCT Patent Application No. PCT/IL2005/000908 filed on Aug. 23, 2005, which is based on and claims the benefit of U.S. Provisional Patent Application No. 60/603,255 filed on Aug. 23, 2004, all of which are incorporated herein in their entirety by this reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 15,789 byte ASCII (text) file named "Seq_List" created on Nov. 1, 2011.

FIELD OF THE INVENTION

The present invention relates to peptides recognized by monoclonal anti-DNA antibodies, the peptides being capable of inhibiting cellular and immune stress responses in a eukaryotic cell, for the treatment of human degenerative disorders and inflammation.

BACKGROUND OF THE INVENTION

Apoptosis

Apoptosis, or programmed cell death, is of fundamental importance to normal biological processes including embryogenesis, maintenance of tissue homeostasis, cellular development of multicellular organisms, elimination of virus-infected cells, and the development of the immune system (Ellis et al., 1991). It is a type of cell death that is fundamentally distinct from degenerative death or necrosis in that it is an active process of gene-directed cellular self-destruction which, in some instances, serves a biologically meaningful homeostatic function.

p53

The p53 protein, originally identified as a tumor-associated antigen, is the product of a tumor suppressor gene that functions to arrest the growth of mutated or aberrant cells (Baker et al, 1990). Functional p53 is believed to detect DNA damage (Lee et al, 1995) and subsequently induce DNA repair (Kastan et al, 1991), growth arrest (Kuerbitz et al, 1992), or apoptosis (Yonish-Rouach et al, 1991) of the aberrant cells. In particular, p53 controls genomic stability by eliminating genetically damaged cells from the cell population, and one of its major functions is to prevent tumor formation.

The p53 protein has at least two DNA-binding sites:
(1) the core of the p53 protein, which interacts specifically with a DNA sequence in the promoter region of p53 responsive genes (el-Deiry et al, 1992); and
(2) the C-terminus of the p53 protein, which can recognize features common to damaged DNA in general (Lee et al, 1995; Foord et al, 1991).

The p53 protein is a transcription factor that binds specifically to a consensus site present in the regulatory sequences of p53-dependent genes (el-Deiry et al, 1992). Mutation of the p53 gene in the domain encoding sequences involved in binding to the specific DNA regulatory site causes a loss of tumor suppression. Therefore, it is not surprising that a significant proportion of natural human tumors bear mutated p53 (Hollstein et al, 1991).

p53 has a short half-life, and, accordingly, is continuously synthesized and degraded in the cell. However, when a cell is subjected to stress, p53 is stabilized. Examples of cell stress that induce p53 stabilization are:
 a) DNA damage, such as damage caused by UV (ultraviolet) radiation, cell mutations, chemotherapy, and radiation therapy;
 b) hyperthermia;
 c) hypoxia; and
 d) deregulation of microtubules caused by some chemotherapeutic drugs, e.g., treatment using taxol or Vinca alkaloids.

Stress-activated p53 induces a cascade of events that result in growth arrest or apoptosis of the stressed cell, thereby preventing the outgrowth of aberrant cells and tumor formation (Ko, 1996). However, excessive activation of p53 after severe stress can be harmful to the organism, as tissue function may be damaged by excessive apoptosis (Komarova, 2001).

Specifically, radiation therapy and chemotherapy exhibit severe side effects, such as severe damage to the lymphoid and hematopoietic system and intestinal epithelia, which limit the effectiveness of these therapies. Other side effects, like hair loss, also are p53 mediated and further detract from cancer therapies. Therefore, to eliminate or reduce adverse side effects in normal tissues associated with cancer treatment, it would be beneficial to inhibit p53 activity in normal tissue during treatment of p53-deficient tumors, and thereby protect normal tissue.

Inactivation of p53 has been considered an undesirable and unwanted event, and considerable effort has been expended to facilitate cancer treatment by restoring p53 function. However, p53 restoration or imitation causes the above-described problems with respect to damaging normal tissue cells during chemotherapy or radiation therapy. These normal cells are subjected to stress during cancer therapy, which leads the p53 in the cell to cause a programmed death. The cancer treatment then kills both the tumor cells and the normal cells.

U.S. Pat. No. 6,593,353 discloses p53 inhibitors in the treatment of p53-mediated diseases, conditions and injuries.

U.S. Pat. No. 6,420,136 discloses methods for modulating the activity of the p53 protein in cells by the addition of a protein which enhances or inhibits the biochemical activity of p53.

U.S. Pat. No. 6,630,584 discloses a single chain antibody which recognizes an epitope exposed on mutant, but not on wild-type p53 and a DNA molecule encoding the single chain Fv, pharmaceutical compositions comprising the antibody and methods of treatment using the pharmaceutical compositions.

p53 and Stress-Associated Response

The adverse effects of p53 activity on an organism are not limited to cancer therapies. p53 is activated as a consequence of a variety of stresses associated with injuries (e.g., burns) naturally occurring diseases (e.g., hyperthermia associated with fever, and conditions of local hypoxia associated with a blocked blood supply, stroke, and ischemia) and cell aging (e.g., senescence of fibroblasts), as well as a cancer therapy. Temporary p53 inhibition, therefore, also can be therapeutically effective in: (a) reducing or eliminating p53-dependent neuronal death in the central nervous system, i.e., brain and spinal cord injury, (b) the preservation of tissues and organs prior to transplanting, (c) preparation of a host for a bone marrow transplant, and (d) reducing or eliminating neuronal damage during seizures, for example.

In addition, various degenerative diseases, including Alzheimer's disease, Parkinson's disease, ischemic stroke (Mattson, 2001; Martin, 2001), glaucoma (Nickells, 1999) secondary degeneration after trauma (Raghupathi, 2000), myocardial infarction (Haunstetter, 1998) are associated with excessive cell death of sensitive tissue in response to stress. Therefore, temporary inhibition of stress-related cell death may serve the prevention and therapy of degenerative diseases (Komarova, 2001).

Monoclonal Antibody to the DNA-Binding Domain of p53

Antibodies to DNA are characteristic of many autoimmune diseases, notably systemic lupus erythematosus (SLE) and particularly lupus nephritis. However, there is at present no generally accepted explanation for the prevalence of anti-DNA antibodies in autoimmune disorders. Immunity to DNA appears to be driven by an antigen (Radic et al, 1994), but self-DNA is unlikely to be the driving antigen because mammalian DNA usually does not induce an anti-DNA immune response (Pisetsky, 1996).

It has been reported that immunization with monoclonal antibodies can induce immune responses that extend beyond the specificity of the antibody, probably by anti-idiotypic connectivity based on idiotypic-determinants in the variable regions of the immunizing monoclonal antibody.

According to idiotypic antibody network terminology, Ab1 is the first antibody, the antibody binding to the antigen, and Ab2 is the anti-idiotypic antibody to Ab1. The variable region of Ab2 may mimic the conformation of the antigen because both the antigen and Ab2 can be bound by Ab1. Ab3 is the anti-idiotypic antibody to Ab2. Because of the chain of structural complementarity, Ab1 and Ab3 can have similar specificity for the original antigen.

The PAb-421 antibody is a prototypic monoclonal antibody that reacts with the C-terminal DNA-binding domain of p53. The sequences of the variable heavy ($V_H$) and variable light ($V_L$) chains of the anti-p53 PAb-421 have been elucidated (see WO 98/56416). The use of PAb-421 antibody for the treatment of cancer was suggested, since it activated DNA binding of p53 in vitro (see WO 94/12202).

The inventors previously reported that immunization of mice with PAb-421 induced formation of anti-idiotypic antibodies that also bind DNA (Herkel et al., 2000; and WO 00/23082). Two of these monoclonal anti-idiotypic antibodies, designated Idi-1 and Idi-2, mimicked the binding properties of the p53 regulatory domain and reacted specifically with PAb-421 and double- and single stranded DNA.

It was suggested by the present inventors (after the priority date of the present invention) that damaged DNA has a chemically defined structure that is recognized by p53 and by Idi-1 and Idi-2 antibodies (Herkel, et al, 2004). Nowhere in the background art was it taught or suggested that it is possible to identify novel peptides having anti-apoptotic and anti-inflammatory properties using such anti-idiotypic antibodies.

There is an unmet need for novel compositions that may serve to attenuate cellular and immune stress-response in normal tissue, in a manner that is specific, safe and effective, thereby reducing the severity of stress associated degenerative diseases and stress-induced inflammation.

SUMMARY OF THE INVENTION

The present invention provides compositions and methods comprising peptides for inhibiting cellular and immune stress-response to a variety of stress-associated conditions. The peptides of the present invention exhibit anti-apoptotic and anti-inflammatory activity, thereby increasing cell survival in cells or tissues that are exposed to stress.

While the use of antibodies to p53 for inducing anti-tumor immunity has been described, the present invention demonstrates that anti idiotypic antibodies immunoreactive with anti-p53 antibodies also may be used to define therapies useful to prevent or decrease cell death.

Unexpectedly, it is now disclosed that peptides, recognized by monoclonal antibodies generated by idiotypic immunization to an anti-p53 monoclonal antibody are of potential use for therapy of human degenerative diseases and in modifying inflammatory responses. In other words, the anti-p53 antibodies (Abs) can generate anti-idiotypic Abs, wherein these latter Abs recognize epitopes useful for preventing cell death or inflammation.

The invention is based, in part, on experiments demonstrating the efficacy of the peptides of the invention in ameliorating stress-induced cell death and p53-mediated response, induced by stimuli such as DNA-damaging agents, hyperthermia, toxic stress and γ-irradiation.

Surprisingly, it was further discovered that peptides of the invention exhibit anti-inflammatory activity, both in vitro and in vivo. Thus, the invention demonstrates that the peptides of the invention are useful for treating inflammatory and autoimmune diseases.

According to a first aspect, the invention is directed to peptides comprising an epitope immunoreactive with an anti-idiotypic antibody directed against an anti-p53 antibody, wherein the anti-p53 antibody is immunoreactive with at least a part of the regulatory domain at the C-terminus of p53. The peptides of the invention exhibit at least one activity selected from anti-apoptotic activity and anti-inflammatory activity.

In one particular embodiment, the peptides are immunoreactive with an anti-idiotypic antibody directed against the anti-p53 antibody PAb-421 (Herkel et al., 2000, hereby fully incorporated by reference). In other particular embodiments, the peptides are immunoreactive with monoclonal antibodies designated Idi-1 and Idi-2, having structural mimicry properties to the p53 regulatory domain (Herkel et al., 2004, hereby fully incorporated by reference).

In one embodiment, the anti-idiotypic antibody is a molecule comprising $V_L$-CDR3 and $V_H$-CDR3 sequences selected from the group consisting of: SEQ ID NO:15 and 18 and SEQ ID NO:21 and 24. In another embodiment, the anti-idiotypic antibody is a molecule comprising $V_L$ regions and $V_H$ regions selected from the group consisting of SEQ ID NO:9 and 10, SEQ ID NO:11 and 12, analogs and derivatives thereof.

The peptides are characterized and synthesized by methods known in the art. In one embodiment, the peptides are characterized by mass spectrometry and synthesized by chemical synthesis.

According to another embodiment, the peptides may have structural complementarity to the DNA-binding domain of p53. Without wishing to be bound to any particular theory or mechanism of action, it is postulated that the peptides may be capable of binding p53 therefore preventing p53 from binding to damaged-DNA. In another embodiment, the peptides of the invention exhibit the activity of binding a protein involved in apoptosis. In another embodiment the peptides of the invention exhibit the activity of preventing said protein from binding to damaged DNA.

According to certain embodiments the peptide comprises a total of about 5 to 25 amino acids, preferably the peptide comprises from about 5 to about 25 amino acids, preferably from about 7 to 12 amino acids.

In certain particular embodiments, the present invention provides novel peptides having an amino acid sequence selected from the group consisting of SEQ ID NO:1 to SEQ ID NO:4, analogs, derivatives or active fragments thereof having anti-apoptotic activity and/or anti-inflammatory activity. The peptides of the present invention are as follows:

SEQ ID NO:1—LPPLPYP, designated Stressin-1;
SEQ ID NO:2—DLSTDALHYRTA, designated Stressin-2;
SEQ ID NO:3—HPTNQQSLWRWP, designated Stressin-3;
SEQ ID NO:4—SSLSVDYPTRYP, designated Stressin-4.

In other particular embodiments, the derivative is a retro-inverso peptide, having an amino acid sequence as set forth in any one of SEQ ID NOS:5-8:

SEQ ID NO:5—PYPLPPL (all residues in the "D" isomeric form);
SEQ ID NO:6—ATRYHLADTSLD (all residues in the "D" isomeric form);
SEQ ID NO:7—PWRWLSQQNTPH (all residues in the "D" isomeric form);
SEQ ID NO:8—PYRTPYDVSLSS (all residues in the "D" isomeric form).

In one particular embodiment, the peptide has an amino acid sequence as set forth in any one of SEQ ID NOS:1, 2 and 5.

According to other embodiments, the peptides of the present invention are useful for selectively preventing cell death of normal tissue. In one embodiment, the peptides inhibit apoptotic activity of mammalian cells. In another embodiment, the peptides inhibit apoptotic activity of human cells.

According to certain preferred embodiments the peptides of the present invention are capable of inhibiting apoptotic activity by at least 25%, preferably by at least 50%, more preferably by at least 75% and most preferably by at least 95%.

The present invention provides peptides having the ability to effectively inhibit cellular and immune stress responses in normal tissue, and are useful to treat a disease or condition where inhibition of intracellular protein activity provides a benefit.

According to some embodiments the peptides of the invention are useful for treating stress-associated human degenerative diseases. According to other embodiments the peptides are capable of down regulating immune mediated stress responses.

In other aspects, the invention is directed to an antibody molecule comprising $V_L$-CDR3 and $V_H$-CDR3 sequences selected from the group consisting of: SEQ ID NO:15 and 18 and SEQ ID NO:21 and 24, and uses thereof for the isolation of peptides according to the invention. In one embodiment, the antibody molecule comprises $V_L$ regions and $V_H$ regions selected from the group consisting of SEQ ID NO:9 and 10 and SEQ ID NO:11 and 12.

According to yet another aspect the present invention provides a pharmaceutical composition comprising as an active ingredient a peptide of the invention or a salt thereof and a pharmaceutically acceptable carrier or diluent.

According to another aspect the present invention provides a method for modulating cellular and immune stress-associated responses in a cell of an organism comprising exposing the cell to an effective amount of a peptide of the invention, an analog, a derivative, or a salt thereof.

Diseases and inflammatory conditions that may be treated by the peptides of the invention include, but not limited to, Alzheimer's disease, Parkinson's disease, secondary degeneration after trauma, stroke, CNS intoxication, glaucoma, macular degeneration, type 1 diabetes, multiple sclerosis, systemic lupus erythematosis, autoimmune uveitis, graft versus host disease, graft rejection, arthritis, systemic inflammatory response syndrome (SIRS) inflammatory bowel disease (IBD), adult respiratory distress syndrome (ARDS), psoriasis, atherosclerosis, myocardial infarction, radiation disease, hyperthermia, hypoxia, fulminant toxic liver, kidney failure, infertility and many others.

In another aspect, the invention provides a method for treating a degenerative disease or condition in a subject in need thereof, comprising administering to the subject a therapeutically effective amount of a peptide of the invention, an analog, a derivative, or a salt thereof.

In one embodiment, the disease or condition is a stress-associated degenerative disorder.

In another embodiment, said subject has a neoplastic disorder and is undergoing chemotherapy and/or radiation therapy for the treatment of cancer.

In another embodiment, the disease or condition is selected from the group consisting of: Alzheimer's disease, Parkinson's disease, secondary degeneration after trauma, stroke, CNS intoxication, glaucoma, macular degeneration, myocardial infarction, radiation disease, hyperthermia, hypoxia, fulminant toxic liver, kidney failure and infertility.

In another aspect, the invention provides a method for treating an inflammatory disease or condition in a subject in need thereof, comprising administering to the subject a therapeutically effective amount of a peptide of the invention, an analog, a derivative, or a salt thereof.

In one embodiment, the disease or condition has an etiology associated with production of at least one pro-inflammatory cytokine selected from IL-6 and TNF-α.

In another embodiment, the disease is an autoimmune disease.

In other embodiments, the disease or condition is selected from the group consisting of: type 1 diabetes, multiple sclerosis, systemic lupus erythematosis (SLE), autoimmune uveitis, arthritis, systemic inflammatory response syndrome (SIRS) inflammatory bowel disease (IBD), adult respiratory distress syndrome (ARDS), psoriasis, atherosclerosis, graft rejection and graft versus host disease.

In one particular embodiment, the disease is multiple sclerosis.

In one embodiment, the peptide inhibits apoptotic activity in response to cellular and immune stress disorders in normal tissue or cells. According to one embodiment the peptides of the present invention modulate intracellular protein activity within a cell in vivo. In another embodiment, the peptides of the present invention modulate intracellular protein activity within a cell ex vivo.

According to some embodiments the peptide may be administered to the subject in need thereof by any suitable route of administration, including, but not limited to, orally, topically, transdermally, parenterally These and other embodiments of the present invention will become apparent in conjunction with the figures, description and claims that follow.

BRIEF DESCRIPTION OF THE FIGURES

FIG. 7: Amino acid sequences of the variable regions of PAb-421, Idi-1 and Idi-2. Complementarity Determining Regions (CDRs) of the light chain or of the heavy chain are aligned. Presented are Idi-1 VL (SEQ ID NO: 9) and VH (SEQ ID NO: 10); Idi-2 VL (SEQ ID NO: 11) and VH (SEQ ID NO: 12); Idi-1 VL CDR1-3 (SEQ ID NOs: 13-15, respectively) and VH CDR1-3 (SEQ ID NOs: 16-18, respectively); Idi-2 VL CDR1-3 (SEQ ID NOs: 19-21, respectively) and VH CDR1-3 (SEQ ID NOs: 22-24, respectively); and PAb-421 VL (SEQ ID NO: 29), VH (SEQ ID NO: 30), VL CDR1-3 (SEQ ID NOs: 31-33, respectively) and VH CDR1-3 (SEQ ID NOs: 34-36, respectively).

DETAILED DESCRIPTION OF THE INVENTION

Figure 1:
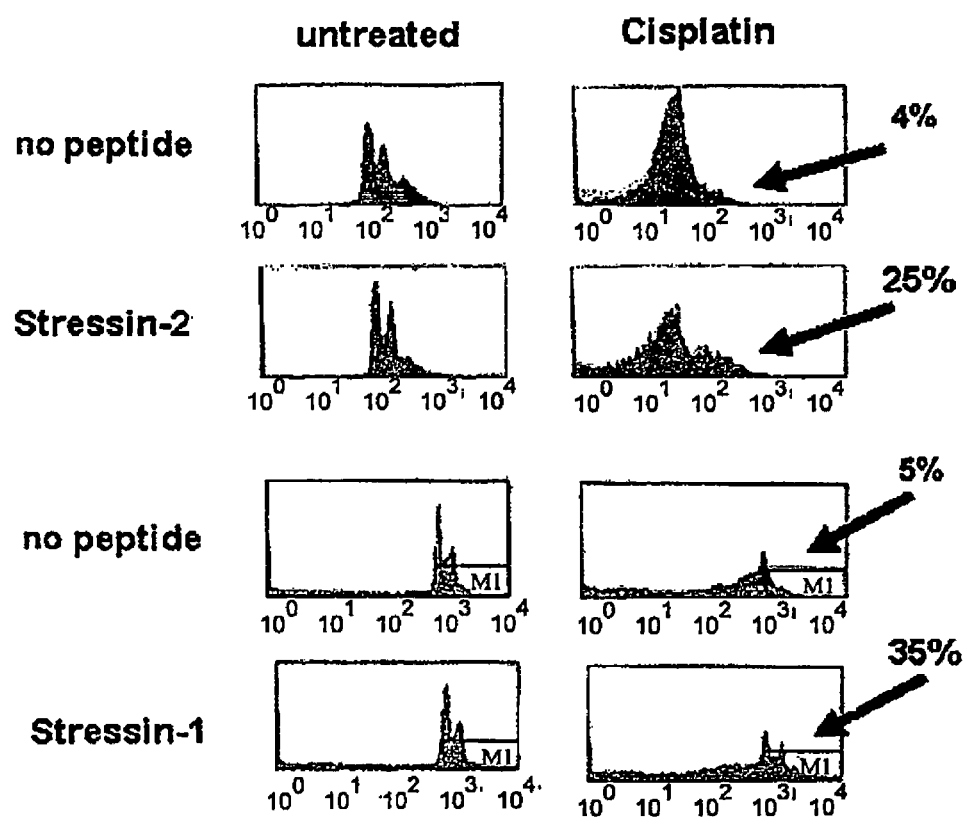
FIG. 1: DNA content of L12 cells treated with the DNA-damaging agent cisplatin, as a measure for p53-mediated cell death.

The present invention provides compositions and methods comprising peptides for inhibiting cellular and immune stress-response to a variety of stress-associated conditions. The invention provides compositions and methods for the treatment of human degenerative diseases and inflammation, utilizing peptides recognized by monoclonal anti-DNA antibodies, the peptides having anti-apoptotic and anti-inflammatory activity.

Definitions

As used herein, the term "Linear Peptide" means a peptide or polypeptide in which the amino acids are linked to one another via an amide bond formed between the alpha-amino group of one and the alpha-carboxylic group of another.

As used herein, "cell" refers to a eukaryotic cell. Typically, the cell is of animal origin and can be a stem cell or somatic cells. Suitable animal cells can be of, for example, mammalian and avian origin. Examples of mammalian cells include human, bovine, ovine, porcine, murine, rabbit cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), cardiac muscle cell, macrophage, dendritic cell, neuronal cell (e.g., a glial cell or astrocyte).

In the context of this invention "modulation" means inhibition; i.e., a decrease in expression. This modulation can be measured in ways which are routine in the art, for example by Western blot or ELISA assay of protein expression, or by an immunoprecipitation assay of protein expression.

The term "treating" as used herein includes prophylactic and therapeutic uses, and refers to the alleviation of symptoms of a particular disorder in a patient, the improvement of an ascertainable measurement associated with a particular disorder, or the prevention of a particular immune response (such as transplant rejection).

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (fragment crystalline) domains. The antigen binding domains, Fab', include regions where the polypeptide sequence varies. The term F(ab')$_2$ represents two Fab' arms linked together by disulfide bonds. The central axis of the antibody is termed the Fc fragment. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1).

The variable domains of each pair of light and heavy chains form the antigen binding site. The domains on the light and heavy chains have the same general structure and each domain comprises four framework regions, whose sequences are relatively conserved, joined by three hypervariable domains known as complementarity determining regions (CDR1-3). These domains contribute specificity and affinity of the antigen binding site.

The term "antibody" as used herein refers to a polypeptide ligand substantially encoded by an immunoglobulin gene or immunoglobulin genes, or fragments thereof, which specifically binds and recognizes an epitope (e.g., an antigen). As used herein, this term refers to intact molecules such as polyclonal antibodies or monoclonal antibodies (mAbs), recombinant and engineered antibodies, as well as to fragments thereof, such as Fab, F(ab')2, Fab miniantibodies (see, for example, U.S. Pat. No. 5,910,573, U.S. Pat. No. 6,294,353, WO 96/37621, U.S. patent application Ser. No. 08/999,554), Fv, scFv (e.g. U.S. Pat. Nos. 4,946,778, 5,091,513 and 5,096, 815) and the like which are capable of binding the epitopic determinant. Antibodies used in the invention can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides are exemplified by bovine serum albumin, thyroglobulin and keyhole limpet hemocyanin. The coupled peptide is then used to immunize the animal (e.g., a mouse, a rat, or a rabbit). Non-limitative methods of generating antibodies are described in the Examples hereinbelow; however, other methods well known in the art may readily be used.

By the term "anti-idiotypic antibody" is intended an antibody directed against (in other words, immunoreactive with) an idiotypic determinant of another antibody. As used herein, the term "idiotypic determinant" refers to an antigenic determinant or epitope unique to the immunoglobulin product of a single clone of cells. The idiotope is found in the variable region of the antibody. The term "epitope" refers to an antigenic determinant on a molecule which is recognized by antibodies.

As used herein, the term "immunoreactive" means that the antibody is capable of binding the antigen with a binding affinity that is indicative of an immune reaction to the antigen. Such affinities are well known to those of skill in the art and include affinities of $10^5$ to $10^{14}$ M. Methods of determining the affinity of an antibody composition are described in Day, Advanced Immunochemistry, ($2^{nd}$ edition) Wiley-Liss, New York, N.Y. (1990).

Stressin Peptides

According to a first aspect, the invention is directed to peptides comprising an epitope immunoreactive with an anti-idiotypic antibody directed against an anti-p53 antibody, wherein the anti-p53 antibody is immunoreactive with at least a part of the regulatory domain at the C-terminus of p53. The peptides of the invention exhibit at least one activity selected from anti-apoptotic activity and anti-inflammatory activity, as will be specified hereinbelow.

In one embodiment, the peptides are selected by anti-idiotypic monoclonal antibodies having structural mimicry properties to the p53 regulatory domain. According to certain embodiments, the peptides are immunoreactive with monoclonal antibodies raised against anti-p53 antibodies. In one particular embodiment, the anti-p53 antibody is PAb-421 (Herkel et al., 2000). In other particular embodiments, the peptides are immunoreactive with monoclonal antibodies designated Idi-1 and Idi-2, having structural mimicry properties to the p53 regulatory domain (Herkel et al., 2004).

In other embodiments, the peptides are immunoreactive with an anti-idiotypic antibody molecule comprising $V_L$-CDR3 and $V_H$-CDR3 sequences selected from the group consisting of: SEQ ID NOS:15 and 18, and SEQ ID NOS:21 and 24. In another embodiment, the anti-idiotypic antibody is a molecule comprising CDR sequences selected from the group consisting of: SEQ ID NOS:13-18, and SEQ ID NOS: 19-24. In another embodiment, the anti-idiotypic antibody is a molecule comprising $V_L$ regions and $V_H$ regions selected from the group consisting of SEQ ID NOS:9 and 10, SEQ ID NOS:11 and 12, analogs thereof.

The peptides are characterized and synthesized by methods known in the art. In one embodiment, the peptides are characterized by mass spectrometry and synthesized by chemical synthesis, as described below.

The peptides of the invention are preferably from 5 to 25 amino acids, more preferably from 5 to 15 amino acids and most preferably from 7 to 12 amino acids.

According to certain particular embodiments, the present invention provides four selected peptides, designated Stressin-1 to 4 (for STress RESponse Specific peptide INhibitor). The amino acid sequences of certain peptides of the invention are listed in Table 1 and designated SEQ ID NO:1 through SEQ ID NO:4.

Unless otherwise specified, the amino acid residues described herein are preferred to be in the "L" isomeric form. However, residues in the "D" isomeric form can be substituted for any L-amino acid residue, as long as the peptide retains the desired functional property.

In other particular embodiments, the invention provides analogs, fragments and functional derivatives of the peptides designated SEQ ID NO:1 through SEQ ID NO:4, as will be described in detail hereinbelow. According to certain particular embodiments, the derivatives are retro-inverso peptides having an amino acid sequence as set forth in any one of SEQ ID NOS:5-8, as specified below. In a particular embodiment, the peptide has an amino acid sequence as set forth in any one of SEQ ID NOS:1, 2 and 5.

Previously, mAbs Idi-1 and Idi-2 were demonstrated to specifically bind both PAb-421 and DNA, single- or double-stranded (Herkel et al., 2000 of some of the inventors of the present invention). The present invention provides antibody molecules directed to PAb-421 comprising variable regions selected from the group consisting of SEQ ID NOS:9 and 10 and SEQ ID NOS:11 and 12, and antibody molecules comprising CDRs having amino acid sequences selected from the group consisting of: SEQ ID NOS:13-18 and SEQ ID NOS: 19-24. Such antibodies exclude the known mAbs termed Idi-1 and Idi-2.

In one embodiment, the antibody molecule comprises $V_L$-CDR3 and $V_H$-CDR3 sequences selected from the group consisting of: SEQ ID NOS:15 and 18 (corresponding to Complementarity Determining Region 3 of the light chain of Idi-1 and Complementarity Determining Region 3 of the heavy chain of Idi-1, respectively) and SEQ ID NOS:21 and 24 (Idi-2). In another embodiment, the antibody molecule comprises CDR sequences as presented in Table 4 below, having amino acid sequences selected from the group consisting of: SEQ ID NOS:13-18 (Idi-1) and SEQ ID NOS:19-24 (Idi-2). In another embodiment, the antibody molecule comprises $V_L$ regions and $V_H$ regions (variable regions of an immunoglobulin light and heavy chain) selected from the group consisting of SEQ ID NOS:9 and 10 (Idi-1), SEQ ID NOS:11 and 12 (Idi-2). The antibody molecules of the invention also include molecules comprising analogs and derivatives of said $V_L$ regions and $V_H$ regions, as long as the analog or derivative is immunoreactive with the antigen-binding portion of PAb-421.

In another aspect, the invention provides use of antibody molecules as described above for isolating peptides exhibiting at least one activity selected from the group consisting of anti-apoptotic activity and anti-inflammatory activity. Suitable methods utilizing these antibodies for identification and isolation of the peptides of the invention are disclosed hereinbelow.

Phage Display Library

Phage display peptide libraries have emerged as a powerful method in identifying such peptide agonists and antagonists. See, for example, Scott et al. (1990), Devlin et al. (1990), U.S. Pat. No. 5,223,409; U.S. Pat. No. 5,733,731; U.S. Pat. No. 5,498,530; U.S. Pat. No. 5,432,018; U.S. Pat. No. 5,338,665; U.S. Pat. No. 5,922,545; WO 96/40987; and WO 98/15833. In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. See, e.g., Cwirla et al. (1997), in which two distinct families were identified. The peptide sequences may also suggest which residues may be safely replaced by alanine scanning or by mutagenesis at the DNA level. Mutagenesis libraries may be created and screened to further optimize the sequence of the best binders (Lowman, 1997).

The peptides of the invention were selected and isolated from a phage display library (Ph.D.-7 or Ph.D.-12 from New England Biolabs, Frankfurt, Germany) with an antibody surrogate of the p53 regulatory domain. The p53 antibody surrogate had been generated by idiotypic immunization to the PAb-421 monoclonal antibody (Herkel et al., 2000) which binds the p53 regulatory domain; two monoclonal antibodies, designated Idi-1 and Idi-2, mimicked the binding properties of the p53 regulatory domain.

The selected candidate peptides were tested for their ability to interfere with the p53-mediated cellular stress response by testing their capacity to inhibit the response to hyperthermia of the L12 cell line (Wolf, 1984), which lacks endogenous p53 activity and had been stably transfected with the p53 gene or a control vector. In these cells, p53 activity induces growth arrest and cell survival rather than apoptosis in response to hyperthermia (Nitta, 1997).

Four peptides, designated Stressin-1 to -4 (for STress RESponse Specific peptide INhibitor), were identified that at concentrations of 100 μg/ml inhibited p53-mediated growth arrest after hyperthermia and induced death of almost all cells with active p53, which is the response of L12 cells that lack p53 activity (Table 1); the peptide sequences are shown in Table 2.

Alternative Methods for Identifying and Isolating Peptides

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed (see, e.g., Takasaki et al., 1997). These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in E. coli. Another E. coli-based method allows display on the cell's outer membrane by fusion with a peptidoglycan-associated lipoprotein (PAL). Hereinafter, these and related methods are collectively referred to as "E. coli display". In another method, translation of random RNA is halted prior to ribosome release, resulting in a library of polypeptides with their associated RNA still attached. Hereinafter, this and related methods are collectively referred to as "ribosome display". Other methods employ chemical linkage of peptides to RNA; see, for example, Roberts and Szostak (1997). Hereinafter, this and related methods are collectively referred to as "RNA-peptide screening". Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening". Chemical-peptide screening may be advantageous in that it allows use of D-amino acids and other unnatural analogues, as well as non-peptide elements. Both biological and chemical methods are reviewed in Wells and Lowman (1992).

Phage display, in particular, is useful in generating peptides for use in the present invention. It has been stated that affinity selection from libraries of random peptides can be used to identify peptide ligands for any site of any gene product (Dedman et al., 1993). Phage display is particularly well suited for identifying peptides that bind to such proteins of interest as cell surface receptors or any proteins having linear epitopes (Wilson et al., 1998; Kay et al., 1998).

Synthesis of Peptides of the Invention

The peptides of the invention can be produced by any known chemical and recombinant methods of producing an amino-acid sequence, including peptidomimetic methodologies (Allen G., 1989; Young, 1963; Meienhofer, 1973; Schroder and Lupke, 1965). Chemical synthesis is commonly performed by coupling of the amino acid residues or peptide fragments to one another in correct order in liquid phase to produce the desired peptide. Another common strategy is the coupling of the amino acids to one another starting with a solid phase (resin) to which the C-terminal of the last amino acid of the sequence is coupled, whereupon the C-terminal of the penultimate amino acid is coupled to the N-terminal of the last amino acid, etc., finally releasing the built-up peptide from the solid phase (so called solid-phase technique).

The term "peptide" refers to molecules of 2 to 25 amino acids, with molecules of 5 to 20 amino acids preferred and those of 7 to 12 amino acids most preferred. Exemplary peptides may be randomly generated by any of the methods cited above, carried in a peptide library (e.g., a phage display library), or derived by digestion of proteins.

The present invention encompasses any analog, derivative, and conjugate containing the peptides of the invention, the amino acid sequence of which is shown herein so long as the peptide is capable of inhibiting apoptosis and/or inflammation. Thus, the present invention encompasses peptides containing non-natural amino acid derivatives or non-protein side chains.

The term "analog" includes any peptide or polypeptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

A peptide derivative refers to a molecule comprising the amino acid sequence of a peptide of the invention subject to various changes, including, but not limited to, chemical modifications, substitutions, insertions, extensions and deletions where such changes do not destroy the anti-inflammatory or anti-apoptotic activity of the peptide, and such derivative is not a known peptide or protein. "Peptide derivative" is intended to include peptide mimetics, as described hereinbelow. In this regard, a peptide of this invention corresponds to, and preferably is identical to, one of the peptides listed in Table 1, where one or more changes are made so long as the polypeptide retains the inhibitory function of peptide of the invention in one or more of the assays as defined herein. With respect to the antibody molecules of the invention, a variable region derivative retains the ability to specifically bind (i.e. is immunoreactive with) the idiotypic determinant of PAb-421.

Peptide derivatives having chemical modifications include, for example, peptides having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-$NH_2$ acylation, acetylation, or thioglycolic acid amidation, and by terminal-carboxyl-amidation, e.g., with ammonia, methylamine, and the like.

Peptides of the present invention also include any peptide having one or more additions and/or deletions of residues relative to the sequence of the peptides of the invention, the sequence of which are shown herein, so long as the requisite inhibitory activity on apoptosis and/or inflammation is maintained. The term "active fragment" thus relates to a peptide portion of a full length Stressin peptide of the invention that has at least one activity that is characteristic of the corresponding full-length peptide. Non-limiting examples of suitable methods for measuring inhibition of apoptosis and inflammation are demonstrated herein.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

A peptide of the invention may also be conjugated to itself or aggregated in such a way as to produce a large complex containing the peptide. Such large complex may be advantageous because it has new biological properties such as longer half-life in circulation or greater activity.

Peptide Mimetic

Peptidomimetics are small molecules that can bind to proteins by mimicking certain structural aspects of peptides and proteins. They are used extensively in science and medicine as agonists and antagonists of protein and peptide ligands of cellular and other receptors, and as substrates and substrate analogs for enzymes.

A primary goal in the design of peptide mimetics has been to reduce the susceptibility of mimics to cleavage and inactivation by peptidases. In one approach, one or more amide bonds have been replaced in an essentially isosteric manner by a variety of chemical functional groups, including, but not limited to urea bond, carbamate bond, sulfonamide bond, hydrazine bond, or any other covalent bond. In another approach, a variety of uncoded or modified amino acids such as D-amino acids and N-methyl amino acids have been used to modify mammalian peptides.

To test whether Stressin peptide may protect an organism from death by excessive p53 activation and tissue failure by subjecting BALB/c mice to whole body 7-irradiation (6.5 Gy). A retro-inverso peptide was used to determine whether prolonged in vivo half-life would give an advantage (see Example 6); retro-inverso peptides are resistant to proteases and consist of D-amino acids in reversed order, resulting in an altered peptide backbone but unchanged orientation of the side chains (Van Regenmortel, 1998).

As used herein, the term "retro-inverso peptide" of the Stressin-1 peptide, for example, as used in a variation of the invention, is intended to encompass peptides in which the sequence of the amino acids is reversed as compared to the sequence in Stressin-1 and consist of D-amino acids in reversed order.

The present invention thus provides retro-inverso Stressin peptides having an amino acid sequence as set forth in any one of SEQ ID NOS:5-8.

The backbone can comprise a variety of atom types, including carbon, nitrogen, oxygen, sulfur and phosphorus, with the majority of the backbone chain atoms typically consisting of carbon. A plurality of side chain moieties that include a terminal guanidino or amidino group are attached to the backbone. Although spacing between adjacent sidechain moieties is typically consistent, the delivery-enhancing transporters used in the invention can also include variable spacing between sidechain moieties along the backbone.

Cell Death and p53 Inhibition

Apoptosis, or "programmed cell death", is a process whereby the cell executes a "cell suicide" program. It is now thought that the apoptosis program is evolutionarily conserved among virtually all multicellular organisms, as well as among all the cells in a particular organism. Further, it is believed that in many cases, apoptosis may be a "default" program that must be actively inhibited in healthy surviving cells.

The decision by a cell to submit to apoptosis may be influenced by a variety of regulatory stimuli and environmental factors (Thompson, 1995). Physiological activators of apoptosis include tumor necrosis factor (TNF), Fas ligand, transforming growth factor-β, the neurotransmitters glutamate, dopamine, N-methyl-D-aspartate, withdrawal of growth factors, loss of matrix attachment, calcium and glucocorticoids. Damage-related inducers of apoptosis include heat shock, viral infection, bacterial toxins, the oncogenes myc, rel and E1A, tumor suppressor p53, cytolytic T-cells, oxidants, free radicals and nutrient deprivation (antimetabolites). Therapy-associated apoptosis inducers include gamma radiation, UV radiation and a variety of chemotherapeutic drugs, including cisplatin, doxorubicin, bleomycin, cytosine arabinoside, nitrogen mustard, methotrexate and vincristine. Toxin-related inducers or apoptosis include ethanol and d-amyloid peptide. Apoptosis can have particularly devastating consequences when it occurs pathologically in cells that do not normally regenerate, such as neurons. Because such cells are not replaced when they die, their loss can lead to debilitating and sometimes fatal dysfunction of the affected organ. Such dysfunction is evidenced in a number of neurodegenerative disorders that have been associated with increased apoptosis, including Alzheimer's disease, Parkinson's disease, amyotrophic lateral sclerosis, retinitis pigmentosa and cerebellar degeneration.

In one aspect, this invention provides compositions and methods for preventing or inhibiting apoptosis in eukaryotic cells. Irrespective of the mechanism by which the peptides of the invention mediates stress responses, and without wishing to be bound by any theory or mechanism of action, it is postulated that the peptides may be capable of binding p53 therefore preventing p53 to be bound to damaged-DNA.

A potential therapeutic inhibitor of p53 is a compound that acts at any stage of the p53 signaling pathway, and leads to functional inactivation of a p53-mediated response (i.e., blocking of p53-dependent growth arrest, apoptosis, or both). Prior investigators did not consider therapeutic p53 inhibitors because therapeutic p53 suppression was considered a disadvantage leading to the onset and proliferation of cancerous tumors. The present invention, therefore, is directed to the therapeutic and reversible inhibition of p53 activity, and to peptides capable of such inhibition.

However, there are several objectives that should be mentioned before a therapy involving suppression of p53 or any other protein that plays a role in apoptosis or inflammation-related disorders is implemented, for example:

a) providing an inhibitor that is sufficiently efficacious in vivo for practical administration as a therapeutic drug;

b) providing an inhibitor that has a sufficiently low toxicity for use in therapy, and also does not cause undesirable side effects at concentrations sufficient to inhibit p53 activity;

c) exhibiting inhibition that is reversible. Long-term p53 inactivation, for example, can significantly increase the risk of cancer;

d) during temporary p53 inactivation, the cells should recover from the applied stress and the p53-activating signal should be eliminated or reduced, otherwise restoration of p53 activity while the p53-activating signal is active could result in cell damage;

e) the p53 suppression therapy is not associated with a dramatic increase in the frequency of cancer development.

The peptides of the invention can be used alone, or, for example, in conjunction with chemotherapy or radiation therapy during cancer treatment, to protect normal cells from p53 programmed death due to stresses inflicted by a cancer treatment or by a disease or trauma. In addition, during chemotherapy, both tumor and normal cells are destroyed. Tumor cells are preferentially killed compared to normal cells, which is the basis of a successful chemotherapy. By administering a therapeutic p53 inhibitor, for example, normal cells are protected, and the dose of the chemotherapeutic agent, therefore, can be increased to more effectively treat the cancer.

It should be understood that the peptides of the present invention do not necessarily act via modulating p53 activity as some of these peptides exhibited anti-apoptotic activity in p53-deficient cell lines and in p53 activity assays.

Methods to Measure Apoptosis

Apoptosis is an active, gene-directed self-destruction process of the cell and is associated with characteristic morphological and biochemical changes. Nuclear and cytoplasmic condensation and fragmentation of the dying cell into membrane-bound apoptotic bodies are typical characteristics of apoptosis. Another feature of apoptotic cell death is the chromosomal DNA degradation into oligonucleosomal fragments after the activation of specific nucleases.

By "inhibiting apoptosis" or "inhibits apoptotic activity" is meant any decrease in the number of cells that undergo apoptosis relative to an untreated control (i.e. cells not exposed to the peptides of the invention). Preferably, the decrease is at least 25%, more preferably the decrease is at least 50%, and most preferably the decrease is at least one-fold.

Flow cytometry offers a wide variety of possibilities to measure apoptosis. Different methods have been established and implemented, some which stain on the cell surface and some which stain intracellularly.

One of the first approaches was, beside the observation that apoptotic cells shrink and have higher intracellular granularity, to stain with DNA specific fluorochromes (e.g. propidium iodide [PI], ethidium bromide [EtBr]). As soon as a lethal hit is being induced, the DNA starts to change its profile. Apoptotic DNA not only consists of fragmented DNA (visualized as shorter bands, so called DNA ladder, in an agarose gel) but is also partially digested into single nucleotides, so that fluorochromes, like PI or EtBr, have less DNA to stain (Nicoletti et al., 1991). This is typically observed by a shift to the left, called sub-G1 peak, on the specific fluorochrome detection channel in the FACScan™ (from Becton Dickinson, USA).

Another method is the terminal deoxynucleotidyl transferase (TdT)-mediated endlabeling of the DNA strand breaks (TUNEL). The TUNEL method detects DNA strand breaks in cells undergoing apoptosis. TdT is an enzyme which catalyzes the addition of deoxyribonucleotide triphosphate to the 3'-OH ends of double or single-stranded DNA. Unlike normal cells, apoptotic cell nuclei incorporate exogenous nucleotides (dUTP)-DIG in the presence of TdT. An anti-DIG antibody fragment with a conjugated fluorochrome enables the visualization of apoptotic cells. An increase of apoptotic cells causes a higher number of DNA fragments and consequently a brighter fluorescence. An advantage of this method is the very high specificity (Gavrieli et al., 1992). A disadvantage of this method is that it is expensive and can only be used for a small set of samples, because it is time intensive. Therefore, it is not applicable for large screening programs.

The loss of cell membrane polarity and the presentation of increased amounts of phosphatidyl serine (PS) on the outside of the cell membrane during the early phase of apoptosis has led to yet a new approach. Annexin V is a calcium-dependent phospholipid binding protein with high affinity for PS. The cell membrane integrity is maintained in the early and intermediate phases of apoptosis. Early and intermediate apoptotic cells show increased binding of Annexin-FITC and are mainly negative for PI-staining. Late apoptotic stages and necrotic cells become double positive, because of PS presentation on the surface and the PI staining of intracellular nucleic acids due to disintegration of the membrane. This method is also costly and labor intensive.

Other methods for measuring apoptosis in vivo and in vitro are disclosed in U.S. Pat. Nos. 6,726,895 and 6,723,567.

Inflammatory Stress Responses and TNF-α and IL-6 Mediated Inflammation

The mammalian response to stress includes not only the response of the stressed cell, but also the complex activity of the immune system known as inflammation (Nathan et al., 2002), which includes a large number of immune activities that serve tissue maintenance and healing (Cohen, 2000).

Tumor necrosis factor (TNF) and interleukin-6 (IL-6) are important biological entities collectively referred to as pro-inflammatory cytokines. These, along with several other related molecules, mediate the inflammatory response associated with the immunological recognition of infectious agents. The inflammatory response plays an important role in limiting and controlling pathogenic infections.

Elevated levels of pro-inflammatory cytokines are also associated with a number of diseases of autoimmunity such as toxic shock syndrome, rheumatoid arthritis, osteoarthritis, diabetes and inflammatory bowel disease (Dinarello, et al., 1984). In these diseases, chronic elevation of inflammation exacerbates or causes much of the pathophysiology observed.

An important and accepted therapeutic approach for potential drug intervention in these diseases is the reduction of pro-inflammatory cytokines such as TNF (also referred to in its secreted cell-free form as TNF-α) and IL-6. A number of anti-cytokine therapies are currently in clinical trials. Efficacy has been demonstrated with a monoclonal antibody directed against TNF-α in a number of autoimmune diseases (Heath, 1997). These include the treatment of rheumatoid arthritis, Crohn's disease and ulcerative colitis (Rankin, 1997, and Stack et al., 1997). The monoclonal antibody is thought to function by binding to both soluble TNF-α and to membrane bound TNF.

Traumatic brain injury triggers a cascade of events resulting in delayed edema, necrosis and impaired function. Harmful mediators are accumulating in the brain after injury and recently, the role of cytokines in the pathophysiology of brain injury has been suggested. Spatial and temporal induction of TNF-α and IL-6 activity in rat brain after closed head injury has been previously reported. An inhibitor of TNF-α production, HU-211, was shown to improve the outcome of closed brain injury in an experimental model (Shohami, et al., 1997). Atherosclerosis is known to have an inflammatory component and cytokines such as IL-1 and TNF have been suggested to promote the disease.

The pro-inflammatory cytokine IL-6 has been implicated with the acute phase response. IL-6 is a growth factor in a number in oncological diseases including multiple myeloma and related plasma cell dyscrasias (Treon, et al., 1998,). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol et al., 1997). IL-6 also plays a significant role in osteoporosis. In murine models it has been shown to effect bone resorption and to induce osteoclast activity (Ershler et al., 1997).

WO 01/01986 discloses particular compounds alleged to having the ability to inhibit TNF-α. WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease.

The present invention shows that Stressin peptides are useful in interfering and blocking both TNF-α and IL-6 secretion by macrophage cells in response to innate activators such as lipopolysaccharide (LPS) and CpG oligonucleotides (see Example 7). Therefore, these peptides are able to modify the pro-inflammatory signaling pathway in immune cells. As is demonstrated for Stressin-1 below, the peptides of the invention play a role in down-regulating the inflammatory immune response to stress.

The present invention further demonstrates the anti-inflammatory properties of Stressin peptides on autoimmune inflammatory diseases, as exemplified on experimental autoimmune encephalomyelitis (EAE), an animal model of human multiple sclerosis (see Example 8).

Pharmaceutical Compositions and Therapeutic Use

In another aspect, the invention relates to a pharmaceutical composition comprising a therapeutically effective amount of a peptide of the invention and a pharmaceutically acceptable carrier.

As used herein a "pharmaceutical composition" refers to a preparation of one or more of the agents described herein, or physiologically acceptable salts or solvents thereof, with other chemical components such as physiologically suitable carriers and excipients. The purpose of a pharmaceutical composition is to facilitate administration of a compound to an organism.

The preparation of pharmaceutical compositions, which contain peptides or polypeptides as active ingredients is well known in the art. Typically, such compositions are prepared as indictable, either as liquid solutions or suspensions, however, solid forms, which can be suspended or solubilized prior to injection, can also be prepared. The preparation can also be emulsified. The active therapeutic ingredient is mixed with inorganic and/or organic carriers, which are pharmaceutically acceptable and compatible with the active ingredient. Carriers are pharmaceutically acceptable excipients (vehicles) comprising more or less inert substances when added to a pharmaceutical composition to confer suitable consistency or form to the composition. Suitable carriers are, for example, water, saline, dextrose, glycerol, ethanol, or the like and combinations thereof. In addition, if desired, the composition can contain minor amounts of auxiliary substances such as wetting or emulsifying agents and pH buffering agents, which enhance the effectiveness of the active ingredient.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl et al., 1975).

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of compounds or active agents in a single composition or may contain a divided pharmacologically, biologically, therapeutically, or chemically effective amount. The total effective amount can then be administered in cumulative units containing, in total, an effective amount of the active agent.

A therapeutically effective amount of a peptide of the invention is an amount that when administered to a patient is capable of exerting an anti-apoptotic activity and/or an anti-inflammatory activity. Assays for detecting the anti-apoptotic activity of the peptide of the invention include, but are not limited to, staining DNA with specific fluorochromes such as propidium iodide and ethidium bromide, Annexin V assays, TUNEL assays and the like; certain non-limitative examples of such assays are presented in the Examples below. Assays for detecting anti-inflammatory activity of the peptides are also well known in the art; non-limitative examples of such methods are presented in the Examples below.

Although an appropriate dosage of a peptide of the invention varies depending on the administration route, age, body weight sex or conditions of the patient, and should be determined by the physician in the end, the dose suitable for adult humans can generally be between about 0.2-2000 mg/kg body weight, preferably between about 2-200 mg/kg.

The pharmaceutical compositions of the present invention comprises one or more compounds of the present invention, and one or more excipients or diluents. In one embodiment, one or more of the compounds, or solvates, or salts of these compounds.

The term "pharmaceutically acceptable salt" as used herein, refers to salts which are substantially non-toxic to living organisms. Typical pharmaceutically acceptable salts include those salts prepared by reaction of the compounds of the present invention with a pharmaceutically acceptable mineral or organic acid. Such salts are also known as acid addition salts.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen.

The pharmaceutical compositions can be administered locally or systemically by any conventional and appropriate route including, but not limited to, oral, intraperitoneal, parenteral, intravenous, intramuscular, subcutaneous, transdermal, intrathecal, topical, rectal, buccal, inhalational or intranasal.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, like suspending agents, such as sorbitol syrup, methyl cellulose, glucose/sugar syrup, gelatin, hydroxyethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

For administration by inhalation, the peptides for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

The pharmaceutical compositions of the invention are also useful for topical and intralesional application. As used herein, the term "topical" means "pertaining to a particular surface area", e.g. skin and mucosa, and the topical agent applied to a certain area of said surface will affect only the area to which it is applied. The formulations of the peptides/peptide analogs may be administered topically as a gel, ointment, cream, emulsion, sustained release formulation including a transdermal patch, and may comprise liposomes and any other pharmaceutically acceptable carrier suitable for administration of the drug topically. The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

In another aspect, the invention provides a method for modulating cellular and immune stress-associated responses in a cell of an organism comprising exposing the cell to an effective amount of a peptide of the invention.

In other aspects, the present invention relates to methods of treating or preventing the symptoms of inflammatory conditions and/or degenerative diseases and disorders, comprising administering to a patient suffering from the disease a therapeutically effective amount of a peptide of the invention. Yet another aspect of the present invention is to provide a method of reducing or eliminating death of normal cells attributable to trauma or a disease comprising administering a therapeutically effective amount of a peptide according to the invention to an organism to inhibit stress-related protein activity.

In certain embodiments, the peptide is in the form of a pharmaceutical composition comprising an effective amount of said peptide and a pharmaceutically acceptable carrier or diluent.

Stress associated responses are associated with diseases and disorders including, for example, pathological conditions such as neurodegenerative diseases (e.g. stroke, Parkinson's, and Alzheimer's disease), myocardial infarction, exposure to radiation or chemotherapeutic agents, inflammation, injuries (e.g., burns and central nervous system injuries), cell aging, hyperthermia, seizures, hypoxias (e.g., ischemia and stroke), and in transplant tissues and organs prior to transplanting.

These conditions also include autoimmune diseases, characterized by a state of immunization of an individual against at least one of the body's normal constituents. These phenomena are observed in particular in pathologies including, but not limited to infections associated with SLE (Systemic Lupus Erythematosus disease), Gougerot-Sjogren syndrome (or Sjogren's disease) and rheumatoid polyarthritis, as well as pathologies such as sarcoidosis and osteopenia, spondylarthritis, scleroderma, multiple sclerosis, amyotrophic lateral sclerosis, hyperthyroidism, Addison's disease, autoimmune hemolytic anemia, Crohn's disease, Goodpasture's syndrome, Graves' disease, Hashimoto's thyroiditis, idiopathic purpural hemorrhage, insulin-dependent diabetes, myasthenia, pemphigus vulgaris, pernicious anemia, poststreptococcal glomerulonephritis, psoriasis and spontaneous sterility, as well as immediate or delayed phenomena observed during graft rejections and graft-versus host disease. In one particular embodiment, the peptides of the invention are useful for the treatment of multiple sclerosis, as exemplified in Example 8 herein.

The phenomenon of graft rejection is a state of immunization of an individual against foreign constituents (bodily fluids such as blood, cerebrospinal fluid, etc., cells, tissues, organs, antibodies, etc.) deliberately implanted into the patient.

As used herein, the terms "degenerative disorder" "degenerative disease" and "degenerative condition" are directed to any disorder, disease or condition characterized by inappropriate cell proliferation or inappropriate cell death or in some cases, both, or aberrant or disregulated apoptosis. These conditions also include conditions in which, although appropriate and regulated at the level of a single cell, excessive apoptosis is associated with organ dysfunction or failure.

In one embodiment, the peptides are useful to prevent cell death in non-malignant tissue or cells in a subject having a neoplastic disorder and undergoing chemotherapy and/or radiation therapy for the treatment of cancer.

The terms "inflammatory disease" and "inflammatory condition", as used herein, mean any disease or condition in which an excessive or unregulated inflammatory response leads to excessive inflammatory symptoms, host tissue damage, or loss of tissue function.

In one embodiment, the inflammatory disease or condition is an autoimmune disease. In a particular embodiment, the autoimmune disease is multiple sclerosis.

In another embodiment, the inflammatory disease or condition has an etiology associated with production of at least one pro-inflammatory cytokine selected from IL-6 and TNF-α, as discussed herein.

The following examples are to be considered merely as illustrative and non-limiting in nature. It will be apparent to one skilled in the art to which the present invention pertains that many modifications, permutations, and variations may be made without departing from the scope of the invention.

EXAMPLES

Example 1

Peptide Selection from Phage Display Libraries

The monoclonal anti-PAb-421 antibodies Idi-1 and Idi-2 were generated and characterized as described (Herkel et al., 2004). Briefly, BALB/c mice were immunized three times with PAb-421 and the spleen cells of the mouse that produced the highest anti-PAb-421 titers were fused with NSO myeloma cells. Supernatants of the growing cells were screened by ELISA for binding to PAb-421 and to DNA. The hybridomas Idi-1 and Idi-2 were isolated and cloned twice by limiting dilution.

Ph.D.-7 or Ph.D.-12 libraries from New England Biolabs, Frankfurt, Germany were screened according to manufacturers instructions. Briefly, three rounds of selection by Idi-1 or Idi-2 monoclonal antibodies were performed and consensus peptide sequences were identified by sequencing of phage DNA. Candidate peptides were then synthesized by Sigma-Genosis (Pampisford, UK) and further studied in functional assays, as described hereinbelow.

Example 2

Examining the Effect of Candidate Peptides on p53-Mediated Growth Arrest

The selected candidate peptides were tested for their ability to interfere with the p53-mediated cellular stress response by testing their capacity to inhibit the response to hyperthermia of the L12 cell line (Wolf, 1984), which lacks endogenous p53 activity and had been stably transfected with the p53 gene or a control vector. In these cells, p53 activity induces growth arrest and cell survival rather than apoptosis in response to hyperthermia (Nitta, 1997).

The amount of cell death was assessed by staining the cells with the vital dye trypan blue (Sigma) and counting the ratio of dead/live cells per visual field with a light microscope.

Results:

incubation for 2 hours at 42° C. induced death of all cells that lacked p53 and, in contrast, transient growth arrest and survival of about 80% of the cells with active p53. Four peptides, designated Stressin-1 to −4 (for STress RESponse Specific peptide INhibitor), were identified that at concentrations of 100 μg/ml inhibited p53-mediated growth arrest after hyperthermia and induced death of almost all cells with active p53, which is the response of L12 cells that lack p53 activity (Table 1); the peptide sequences are shown in Table 2.

TABLE 1

Incidence of cell death induced by hyperthermia in L12 cells with or without active p53 and inhibition of the p53-dependent stress response by Stressin peptides.

| | no peptide | Stressin 1 | Stressin 2 | Stressin 3 | Stressin 4 |
|---|---|---|---|---|---|
| L12 without p53 | 100% | n.d. | n.d. | n.d. | n.d. |
| L12 with p53 | 20% | 100% | 90% | 80% | 80% |

TABLE 2

Amino acid sequences of Stressin peptides that modify the cellular response to stress.

| SEQ ID NO: | Amino acid sequence | Name |
|---|---|---|
| 1 | LPPLPYP | Stressin-1 |
| 2 | DLSTDALHYRTA | Stressin-2 |
| 3 | HPTNQQSLWRWP | Stressin-3 |
| 4 | SSLSVDYPTRYP | Stressin-4 |

Example 3

Effect of Stressin Peptides on p53-Mediated Cell Death Induced by DNA Damage

L12 cells were treated for 48 hours with 50 μM of the DNA-damaging agent Cisplatin and p53-mediated cell death was determined by measuring the DNA content of cells stained with propidium iodide (FIG. 1). Cells incubated in the absence of peptide responded to Cisplatin treatment with p53-mediated cell death.

Results:

FACS analysis shows that treatment with Stressin-1 or Stressin-2 rescued 35% or 25% of the cells, respectively, from p53-mediated cell death.

Example 4

Effect of Stressin Peptides on p53-Mediated Cell Death in Non-Transformed Cells

Mouse embryo fibroblasts (MEF) were treated with cisplatin (80 μM) in the presence or absence of Stressin-1 peptide as described in Example 3, and cell death was assessed by incorporation of the vital dye Neutral red (Sigma, Taufkirchen, Germany), O.D. at 540 nm was read in an ELISA reader.

Figure 2A:
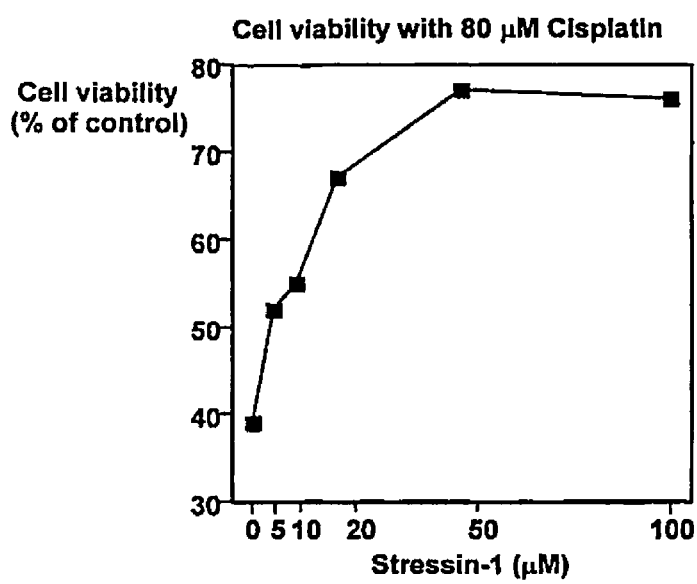
FIG. 2: Cisplatin (80 μM)-induced p53-mediated cell death of mouse embryo fibroblasts.

The percent of viable cells is presented in FIG. 2A; viability was calculated by the equation:

Cell viability=sample $OD_{540} \times 100/OD_{540}$ of untreated cells.

Figure 2B:
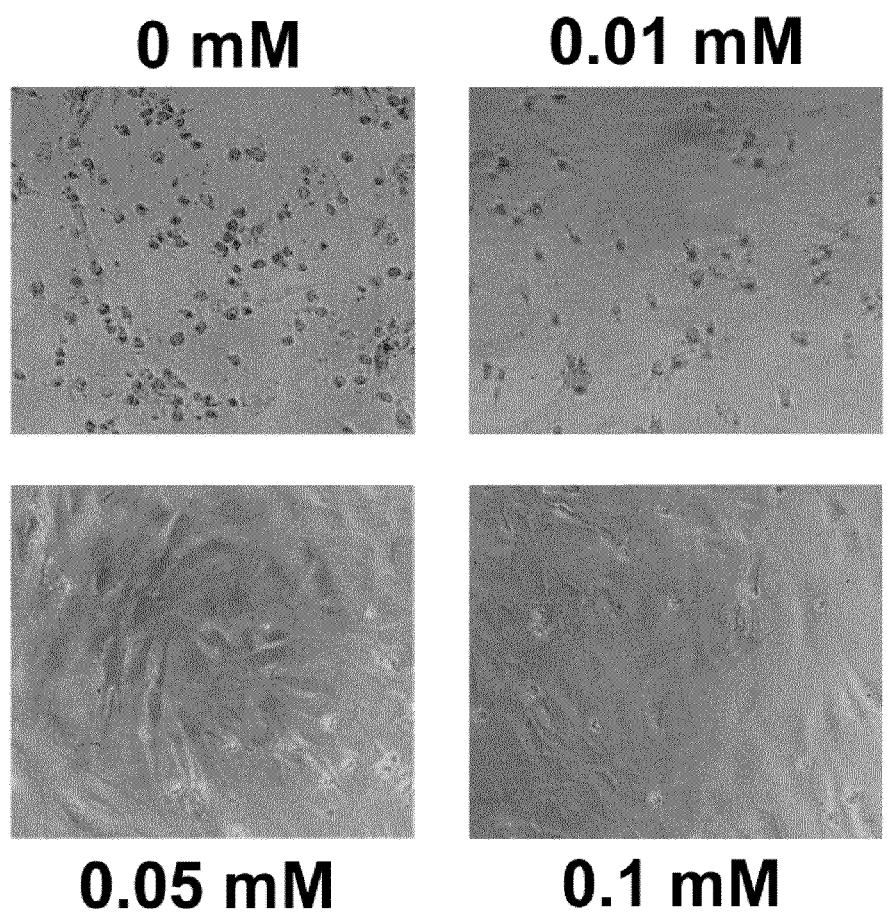

Micrographs of the treated cells are presented in FIG. 2B. FIG. 2 shows that Stressin-1 inhibited cell death of MEF cells induced by 80 μM Cisplatin in a dose-dependent way with maximal efficiency at a concentration of 50 μM.

Example 5

Effect of Stressin Peptides on Cell Death Induced by Toxic Stress

To learn whether Stressin peptide may protect from toxic stress, primary hepatocyte cultures were incubated with or without ethanol at a concentration of 0.6%, and with 50 μM Stressin-1 or without peptide. After 48 hours, the numbers of dead and alive cells were determined by trypan blue exclusion (Table 3).

Results:

All hepatocytes exposed to ethanol died in the absence of Stressin-1; in contrast, Stressin-1 rescued 20% hepatocytes from ethanol-induced cell death.

TABLE 3

Survival of hepatocytes exposed to a lethal
dose of ethanol is promoted by Stressin-1 peptide.

|  | Untreated | Stressin-1 |
|---|---|---|
| Hepatocytes without ethanol | 100% | 100% |
| Hepatocytes with 0.6% ethanol | 0% | 20% |

Example 6

Effect of Stressin Peptides on Mice Subjected to γ-Irradiation

BALB/c mice were subjected to whole body γ-irradiation (6.5 Gy). One hour after irradiation, the mice received intraperitoneally either Stressin-1 (n=7; SEQ ID NO:1) or a modified, retro-inverso Stressin-1 peptide (n=7; SEQ ID NO:5), both at a concentration of 500 µg/mouse, or a sham injection with saline (n=6). The retro-inverso peptide was used to determine whether prolonged in vivo-half-life would give an advantage.

Figure 3:
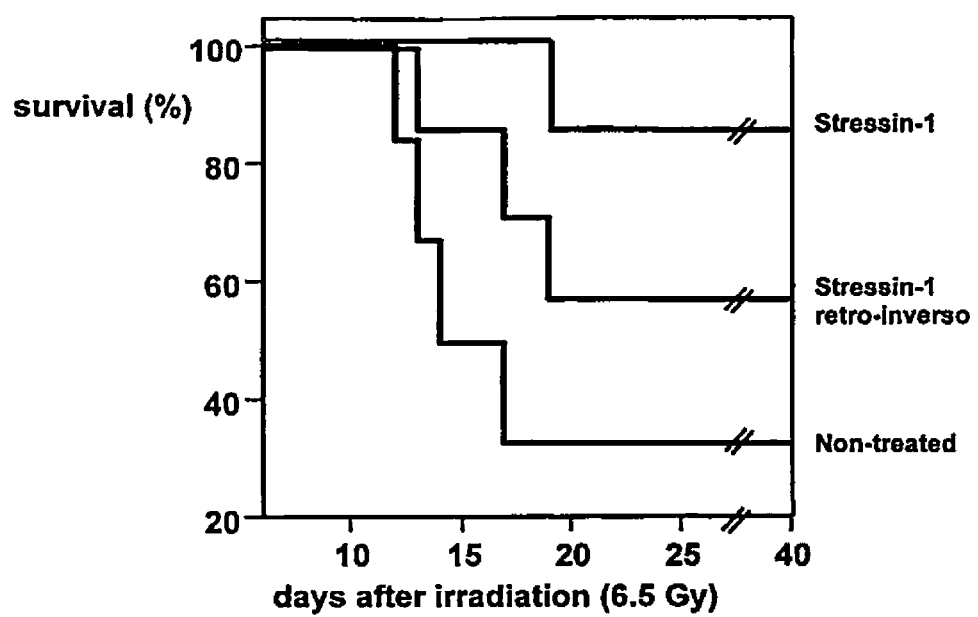
FIG. 3: The effect of Stressin peptides on BALB/c mice when subjected to body irradiation at a dose of 6.5 Gy.

Results:

After 17 days, 66% of the sham-treated group were dead; in contrast, none of the mice treated with the Stressin-1 peptide and only 29% of the mice treated with the modified Stressin-1 peptide were dead. After 40 days only 33% in the sham group recovered from radiation disease; in contrast, 57% and 86% of the mice treated with the modified or the unmodified Stressin-1 peptide recovered from radiation disease (FIG. 3).

Example 7

Effect of Stressin Peptides on LPS- and CpG-Induced Cytokine Secretion

Figure 4:
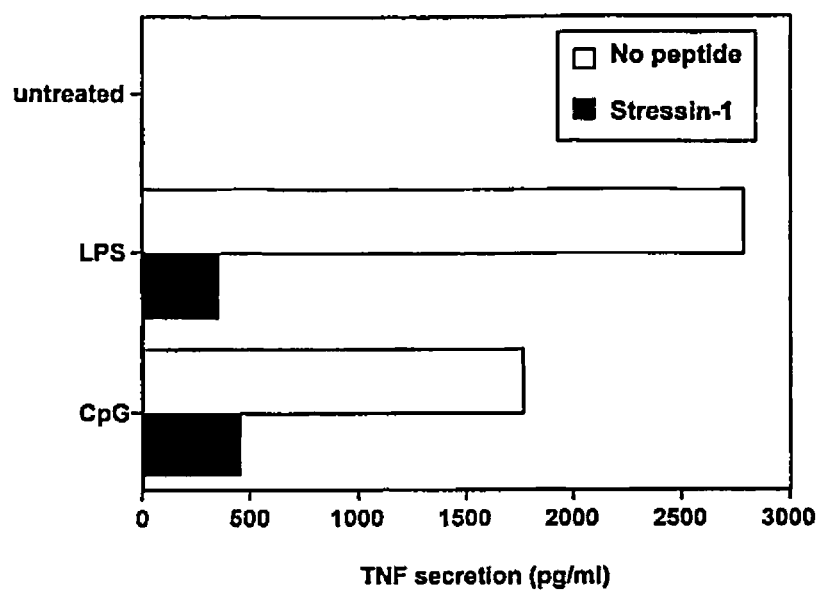
FIG. 4: TNF-α secretion of RAW 264.7 macrophages in response to lipopolysaccharide (LPS) or CpG-oligonucleotides is inhibited by Stressin-1.
Figure 5:
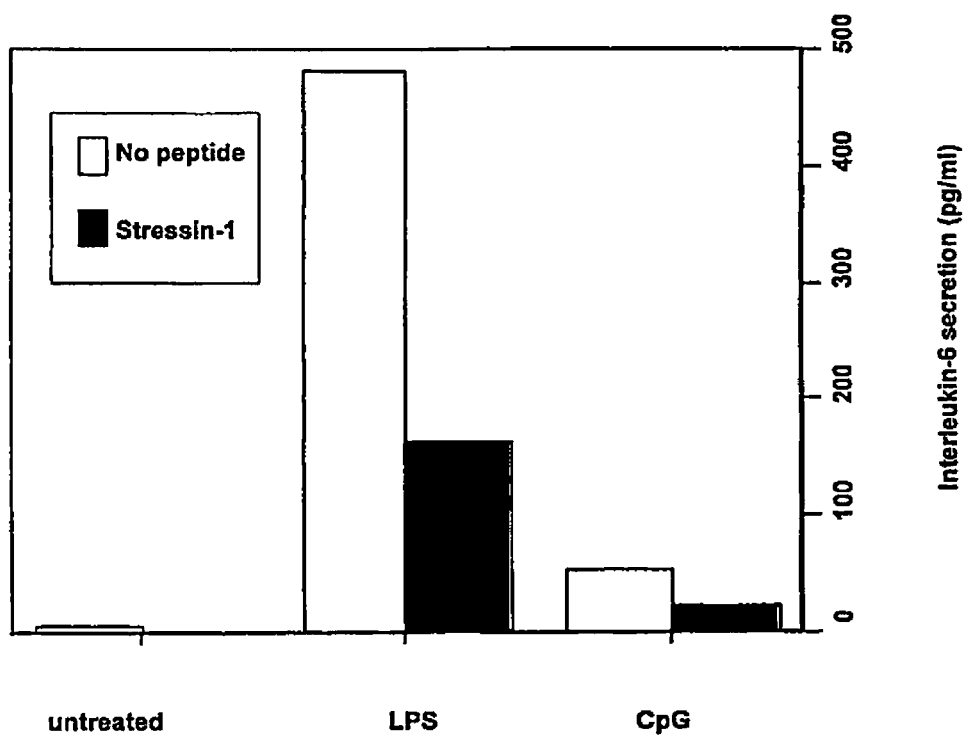
FIG. 5: Interleukin-6 secretion of RAW 264.7 macrophages in response to lipopolysaccharide (LPS) or CpG-oligonucleotides is inhibited by Stressin-1.

To learn whether Stressin peptides may modify the inflammatory response to stress signals, the response of RAW 264.7 macrophage line cells to pro-inflammatory microbial signals, lipopolysaccharide (LPS) and CpG oligonucleotides, was studied. The cells were incubated with LPS or CpG oligonucleotides in the presence or absence of Stressin-1 (50 µM). After 6 hours, the amounts of secreted TNF-α (FIG. 4) or Interleukin-6 (FIG. 5) in culture supernatant, as a measure for macrophage activation, were determined by specific ELISA reagents and anti-TNF-α and anti-IL-6 antibodies (R&D Systems, Wiesbaden, Germany).

Results:

Stressin-1 inhibited macrophage activation and secretion of TNF-α and Interleukin-6 induced by both LPS and CpG oligonucleotides.

Example 8

Stressin-1 Protects Mice from Experimental Autoimmune Disease (EAE)

Figure 6:
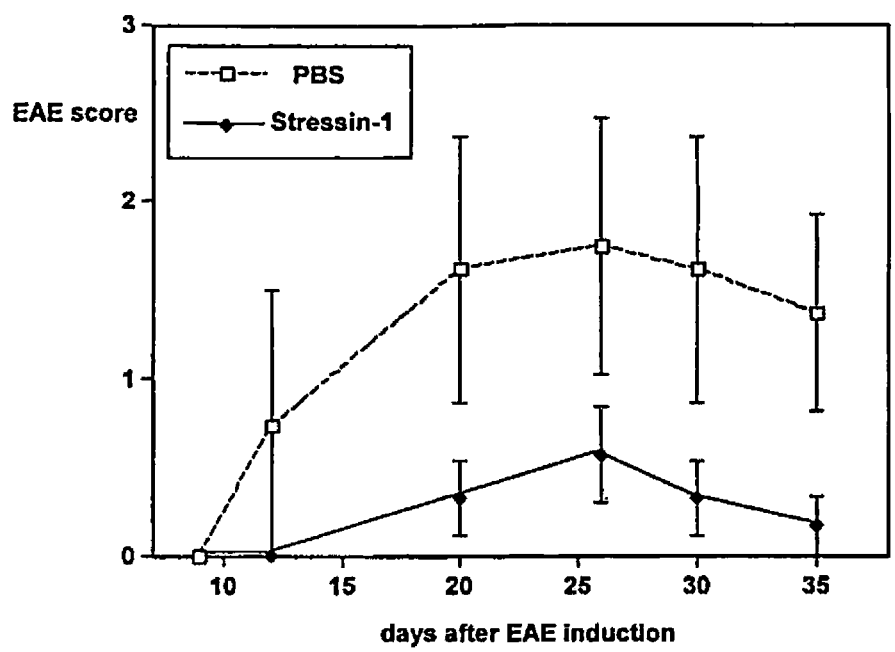
FIG. 6: Inhibitory effect of Stressin-1 in development of experimental autoimmune disease (EAE) in mice.

MBP Ac1-9-specific T cell receptor-transgenic Tg4 mice (Liu et al., 1995) were immunized subcutaneously with 200 µg of modified (Y at position 4) Ac1-9 peptide in complete Freund's Adjuvant followed by intraperitoneal administration of 200 ng of Pertussis toxin the next day. At one hour after MBP immunization one group of mice (n=4) received 100 µl of PBS intraperitoneally and another group of mice (n=6) received 500 µg Stressin-1 peptide in 100 µl PBS intraperitoneally. The mice were then tested for the development of experimental autoimmune encephalomyelitis by assessment of the clinical EAE score. As can be seen in FIG. 6, Stressin-1 protects mice from EAE.

Example 9

Sequencing of Idi-1 and Idi-2 Variable Regions

Total RNA was extracted from Idi-1 and Idi-2 hybridomas using TriReagent (Molecular Research Center, INC.), and the RNA was used as a template for cDNA synthesis using SuperScript Reverse Transcriptase (Invitrogen, Karlsruhe, Germany). PCR amplification of the heavy and light chain variable regions were performed using primers specific for the respective flanking constant region: 5' CGGGAATTC-CCCAGGTGCAGCTGCAGCAGTCTGG SEQ ID NO:25 and 3' GCGGGCCCTCGAGTCTATGTACATATG-CAAGGCTTACAACC SEQ ID NO:26 for the heavy chain; 5' CGCGCAAGCTTGATATTGTGATAACCCAGGATGA SEQ ID NO:27 and 3' GATGGTGGGAAGATG SEQ ID NO:28 for the light chain. PCR products were purified and sequenced using the same primers.

The variable regions of Idi-1 (Idi-1 $V_L$-SEQ ID NO:9; Idi-1 $V_H$-SEQ ID NO:10), Idi-2 (Idi-2 $V_L$-SEQ ID NO:11; Idi-2 $V_H$-SEQ ID NO:12) and PAb-421 are presented in FIG. 7. The CDR sequences of Idi-1 and Idi-2 are indicated in FIG. 1 and listed, along with their corresponding SEQ ID NOS, in Table 4 below:

TABLE 4

CDR sequences of Idi-1 and Idi-2

| SEQ ID NO: | Description | Amino acid sequence |
|---|---|---|
| 13 | Idi-1 $V_L$ CDR1 | RQSLLYKNGKTYLN |
| 14 | Idi-1 $V_L$ CDR2 | LMSIRAS |
| 15 | Idi-1 $V_L$ CDR3 | QQLVEYPYT |
| 16 | Idi-1 $V_H$ CDR1 | KASGYIFTSYWIN |
| 17 | Idi-1 $V_H$ CDR2 | NISPADSSTNYN |
| 18 | Idi-1 $V_H$ CDR3 | EEVRRRRDMDF |
| 19 | Idi-2 $V_L$ CDR1 | QASESVSFAGTSLMH |
| 20 | Idi-2 $V_L$ CDR2 | RASKLES |
| 21 | Idi-2 $V_L$ CDR3 | MQSMEDPYT |
| 22 | Idi-2 $V_H$ CDR1 | KASGYSFTGYTIN |
| 23 | Idi-2 $V_H$ CDR2 | LINPYNGGTCYN |
| 24 | Idi-2 $V_H$ CDR3 | RVWLRRDGFYYAMDY |

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A method for treating amyotrophic lateral sclerosis (ALS) in a subject in need thereof, comprising administering to the subject a therapeutically effective amount of a peptide comprising an epitope immunoreactive with an anti-idiotypic antibody directed against an anti-p53 antibody, wherein the anti-p53 antibody is immunoreactive with at least a part of the regulatory domain of the C-terminus of p53, and wherein the peptide exhibits at least one activity selected from anti-apoptotic activity and anti-inflammatory activity wherein the length of the peptide is 7 to 25 amino acids and has the amino acid sequence as set forth in SEQ ID NO: 1.

2. The method of claim 1, wherein the anti-p53 antibody is PAb-421.

3. The method of claim 1, wherein the amino acid sequence of said peptide is as set forth in SEQ ID NO: 1.

4. The method of claim 1, wherein the peptide is administered to the subject by a route selected from oral, topical, transdermal and parenteral.

* * * * *

SEQUENCE LISTING

```
<160> NUMBER OF SEQ ID NOS: 36

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Leu Pro Pro Leu Pro Tyr Pro
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide

<400> SEQUENCE: 2

Asp Leu Ser Thr Asp Ala Leu His Tyr Arg Thr Ala
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

His Pro Thr Asn Gln Gln Ser Leu Trp Arg Trp Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide

<400> SEQUENCE: 4

Ser Ser Leu Ser Val Asp Tyr Pro Thr Arg Tyr Pro
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: "D" amino acids
<220> FEATURE:
<221> NAME/KEY: MISC_FEATURE
<222> LOCATION: (1)..(1)
<223> OTHER INFORMATION: D-Pro
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Pro
<220> FEATURE:
<221> NAME/KEY: MISC_FEATURE
```

```
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Pro
<220> FEATURE:
<221> NAME/KEY: MISC_FEATURE
<222> LOCATION: (6)..(6)
<223> OTHER INFORMATION: D-Pro
<220> FEATURE:
<221> NAME/KEY: MISC_FEATURE
<222> LOCATION: (7)..(7)
<223> OTHER INFORMATION: D-Leu

<400> SEQUENCE: 5

Pro Tyr Pro Leu Pro Pro Leu
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: "D" amino acids
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (2)..(2)
<223> OTHER INFORMATION: D-Thr
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Tyr
<220> FEATURE:
<221> NAME/KEY: MISC_FEATURE
<222> LOCATION: (5)..(5)
<223> OTHER INFORMATION: D-His
<220> FEATURE:
<221> NAME/KEY: MISC_FEATURE
<222> LOCATION: (6)..(6)
<223> OTHER INFORMATION: D-Leu
<220> FEATURE:
<221> NAME/KEY: MISC_FEATURE
<222> LOCATION: (7)..(7)
<223> OTHER INFORMATION: D-Ala
<220> FEATURE:
<221> NAME/KEY: MISC_FEATURE
<222> LOCATION: (8)..(8)
<223> OTHER INFORMATION: D-Asp
<220> FEATURE:
<221> NAME/KEY: MISC_FEATURE
<222> LOCATION: (9)..(9)
<223> OTHER INFORMATION: D-Thr
<220> FEATURE:
<221> NAME/KEY: MISC_FEATURE
<222> LOCATION: (10)..(10)
<223> OTHER INFORMATION: D-Ser
<220> FEATURE:
<221> NAME/KEY: MISC_FEATURE
<222> LOCATION: (11)..(11)
<223> OTHER INFORMATION: D-Leu
<220> FEATURE:
<221> NAME/KEY: MISC_FEATURE
<222> LOCATION: (12)..(12)
<223> OTHER INFORMATION: D-Asp
```

```
<400> SEQUENCE: 6

Ala Thr Arg Tyr His Leu Ala Asp Thr Ser Leu Asp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: "D" amino acids
<220> FEATURE:
<221> NAME/KEY: MISC_FEATURE
<222> LOCATION: (1)..(1)
<223> OTHER INFORMATION: D-Pro
<220> FEATURE:
<221> NAME/KEY: MISC_FEATURE
<222> LOCATION: (2)..(2)
<223> OTHER INFORMATION: D-Trp
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Trp
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (6)..(6)
<223> OTHER INFORMATION: D-Ser
<220> FEATURE:
<221> NAME/KEY: MISC_FEATURE
<222> LOCATION: (7)..(8)
<223> OTHER INFORMATION: D-Gln
<220> FEATURE:
<221> NAME/KEY: MISC_FEATURE
<222> LOCATION: (9)..(9)
<223> OTHER INFORMATION: D-Asn
<220> FEATURE:
<221> NAME/KEY: MISC_FEATURE
<222> LOCATION: (10)..(10)
<223> OTHER INFORMATION: D-Thr
<220> FEATURE:
<221> NAME/KEY: MISC_FEATURE
<222> LOCATION: (11)..(11)
<223> OTHER INFORMATION: D-Pro
<220> FEATURE:
<221> NAME/KEY: MISC_FEATURE
<222> LOCATION: (12)..(12)
<223> OTHER INFORMATION: D-His

<400> SEQUENCE: 7

Pro Trp Arg Trp Leu Ser Gln Gln Asn Thr Pro His
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: "D" amino acids
<220> FEATURE:
```

```
<221> NAME/KEY: MISC_FEATURE
<222> LOCATION: (1)..(1)
<223> OTHER INFORMATION: D-Pro
<220> FEATURE:
<221> NAME/KEY: MISC_FEATURE
<222> LOCATION: (2)..(2)
<223> OTHER INFORMATION: D-Tyr
<220> FEATURE:
<221> NAME/KEY: MISC_FEATURE
<222> LOCATION: (3)..(3)
<223> OTHER INFORMATION: D-Arg
<220> FEATURE:
<221> NAME/KEY: MISC_FEATURE
<222> LOCATION: (4)..(4)
<223> OTHER INFORMATION: D-Thr
<220> FEATURE:
<221> NAME/KEY: MISC_FEATURE
<222> LOCATION: (5)..(5)
<223> OTHER INFORMATION: D-Pro
<220> FEATURE:
<221> NAME/KEY: MISC_FEATURE
<222> LOCATION: (6)..(6)
<223> OTHER INFORMATION: D-Tyr
<220> FEATURE:
<221> NAME/KEY: MISC_FEATURE
<222> LOCATION: (7)..(7)
<223> OTHER INFORMATION: D-Asp
<220> FEATURE:
<221> NAME/KEY: MISC_FEATURE
<222> LOCATION: (8)..(8)
<223> OTHER INFORMATION: D-Val
<220> FEATURE:
<221> NAME/KEY: MISC_FEATURE
<222> LOCATION: (9)..(9)
<223> OTHER INFORMATION: D-Ser
<220> FEATURE:
<221> NAME/KEY: MISC_FEATURE
<222> LOCATION: (10)..(10)
<223> OTHER INFORMATION: D-Leu
<220> FEATURE:
<221> NAME/KEY: MISC_FEATURE
<222> LOCATION: (11)..(12)
<223> OTHER INFORMATION: D-Ser

<400> SEQUENCE: 8

Pro Tyr Arg Thr Pro Tyr Asp Val Ser Leu Ser Ser
1               5                   10

<210> SEQ ID NO 9
<211> LENGTH: 107
<212> TYPE: PRT
<213> ORGANISM: Artificial Sequence
<220> FEATURE:
<223> OTHER INFORMATION: synthetic peptide

<400> SEQUENCE: 9

Asp Ile Val Ile Thr Gln Asp Glu Leu Ser Asn Pro Val Thr Ser Gly
1               5                   10                  15

Glu Ser Val Ser Ile Ser Cys Arg Gln Ser Leu Leu Tyr Lys Asn Gly
            20                  25                  30

Lys Thr Tyr Leu Asn Trp Phe Leu Gln Arg Pro Gly Gln Ser Pro Gln
        35                  40                  45

Leu Leu Ile Tyr Leu Met Ser Ile Arg Ala Ser Gly Val Ser Asp Arg
    50                  55                  60

Phe Ser Gly Asn Gly Ser Gly Thr Asp Phe Thr Leu Glu Ile Ser Arg
65                  70                  75                  80

Val Arg Ala Glu Asp Val Gly Val Tyr Tyr Cys Gln Gln Leu Val Glu
                85                  90                  95

Tyr Pro Tyr Thr Phe Gly Gly Gly Thr Lys Leu
                100                 105
```

<210> SEQ ID NO 10
<211> LENGTH: 116
<212> TYPE: PRT
<213> ORGANISM: Artificial Sequence
<220> FEATURE:
<223> OTHER INFORMATION: Synthetic peptide

<400> SEQUENCE: 10

```
Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Ile Phe Thr Ser Tyr
            20                  25                  30

Trp Ile Asn Trp Val Arg Gln Arg Pro Gly Gln Gly Leu Glu Trp Ile
        35                  40                  45

Gly Asn Ile Ser Pro Ala Asp Ser Ser Thr Asn Tyr Asn Gln Lys Phe
    50                  55                  60

Lys Asp Lys Ala Thr Leu Thr Val Asp Lys Ser Ser Thr Thr Ala Tyr
65                  70                  75                  80

Met Gln Leu Ser Arg Pro Thr Phe Glu Asp Ser Ala Val Tyr Tyr Cys
                85                  90                  95

Ala Arg Glu Glu Val Arg Arg Arg Asp Met Asp Phe Trp Gly Gln
            100                 105                 110

Gly Thr Ser Val
        115
```

<210> SEQ ID NO 11
<211> LENGTH: 108
<212> TYPE: PRT
<213> ORGANISM: Artificial Sequence
<220> FEATURE:
<223> OTHER INFORMATION: Synthetic peptide

<400> SEQUENCE: 11

```
Asn Ile Val Met Thr Gln Ser Pro Ala Ser Leu Ala Val Ser Leu Gly
1               5                   10                  15

Gln Arg Ala Thr Ile Ser Cys Gln Ala Ser Glu Ser Val Ser Phe Ala
            20                  25                  30

Gly Thr Ser Leu Met His Trp Tyr Gln Gln Lys Pro Gly Gln Pro Pro
        35                  40                  45

Lys Leu Leu Ile Tyr Arg Ala Ser Lys Leu Glu Ser Gly Val Pro Ala
    50                  55                  60

Arg Phe Ser Gly Ser Gly Ser Glu Ser Asp Phe Thr Leu Thr Ile Asp
65                  70                  75                  80

Pro Val Glu Glu Asp Asp Ala Ala Met Tyr Tyr Cys Met Gln Ser Met
                85                  90                  95

Glu Asp Pro Tyr Thr Phe Gly Gly Gly Thr Lys Leu
            100                 105
```

<210> SEQ ID NO 12
<211> LENGTH: 120
<212> TYPE: PRT
<213> ORGANISM: Artificial Sequence
<220> FEATURE:
<223> OTHER INFORMATION: Synthetic peptide

<400> SEQUENCE: 12

```
Gln Val Gln Leu Gln Gln Ser Gly Pro Glu Leu Val Lys Pro Gly Ala
1               5                   10                  15
```

```
Ser Met Lys Ile Ser Cys Lys Ala Ser Gly Tyr Ser Phe Thr Gly Tyr
            20                  25                  30

Thr Ile Asn Trp Val Lys Gln Ser His Gly Lys Asn Leu Glu Trp Ile
        35                  40                  45

Gly Leu Ile Asn Pro Tyr Asn Gly Gly Thr Cys Tyr Asn Pro Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Arg Val Trp Leu Arg Arg Asp Gly Tyr Tyr Ala Met Asp
            100                 105                 110

Tyr Trp Gly Gln Gly Thr Ser Val
            115                 120

<210> SEQ ID NO 13
<211> LENGTH: 14
<212> TYPE: PRT
<213> ORGANISM: Artificial Sequence
<220> FEATURE:
<223> OTHER INFORMATION: Synthetic peptide

<400> SEQUENCE: 13

Arg Gln Ser Leu Leu Tyr Lys Asn Gly Lys Thr Tyr Leu Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Leu Met Ser Ile Arg Ala Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Gln Gln Leu Val Glu Tyr Pro Tyr Thr
1               5

<210> SEQ ID NO 16
<211> LENGTH: 13
<212> TYPE: PRT
<213> ORGANISM: Artificial Sequence
<220> FEATURE:
<223> OTHER INFORMATION: Synthetic peptide

<400> SEQUENCE: 16

Lys Ala Ser Gly Tyr Ile Phe Thr Ser Tyr Trp Ile Asn
1               5                   10

<210> SEQ ID NO 17
<211> LENGTH: 12
<212> TYPE: PRT
<213> ORGANISM: Artificial Sequence
<220> FEATURE:
```

<223> OTHER INFORMATION: Synthetic peptide

<400> SEQUENCE: 17

Asn Ile Ser Pro Ala Asp Ser Ser Thr Asn Tyr Asn
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Glu Glu Val Arg Arg Arg Arg Asp Met Asp Phe
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Gln Ala Ser Glu Ser Val Ser Phe Ala Gly Thr Ser Leu Met His
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Arg Ala Ser Lys Leu Glu Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Met Gln Ser Met Glu Asp Pro Tyr Thr
1               5

<210> SEQ ID NO 22
<211> LENGTH: 13
<212> TYPE: PRT
<213> ORGANISM: Artificial Sequence
<220> FEATURE:
<223> OTHER INFORMATION: Synthetic peptide

<400> SEQUENCE: 22

Lys Ala Ser Gly Tyr Ser Phe Thr Gly Tyr Thr Ile Asn
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic peptide -continued

<400> SEQUENCE: 23

Leu Ile Asn Pro Tyr Asn Gly Gly Thr Cys Tyr Asn
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24

Arg Val Trp Leu Arg Arg Asp Gly Phe Tyr Tyr Ala Met Asp Tyr
1               5                   10                  15

<210> SEQ ID NO 25
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 25
cgggaattcc ccaggtgcag ctgcagcagt ctgg                         34

<210> SEQ ID NO 26
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 26
gcgggccctc gagtctatgt acatatgcaa ggcttacaac c                 41

<210> SEQ ID NO 27
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 27
cgcgcaagct tgatattgtg ataacccagg atga                         34

<210> SEQ ID NO 28
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 28
gatggtggga agatg                                              15

<210> SEQ ID NO 29
<211> LENGTH: 109
<212> TYPE: PRT
<213> ORGANISM: Artificial Sequence
<220> FEATURE:
<223> OTHER INFORMATION: synthetic peptide

<400> SEQUENCE: 29

Asp Ile Gln Leu Thr Gln Ser Pro Leu Thr Leu Ser Val Thr Ile Gly
1               5                   10                  15

```
Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Asn Arg Val Glu Ala Glu Asp Leu Gly Val Tyr Tyr Cys Trp Gln Gly
                85                  90                  95

Thr His Ser Pro Leu Thr Phe Gly Ala Gly Thr Lys Leu
                100                 105

<210> SEQ ID NO 30
<211> LENGTH: 116
<212> TYPE: PRT
<213> ORGANISM: Artificial Sequence
<220> FEATURE:
<223> OTHER INFORMATION: SYNTHETIC PEPTIDE

<400> SEQUENCE: 30

Gln Val Lys Leu Gln Glu Ser Gly Ala Glu Leu Val Arg Ser Gly Ala
1               5                   10                  15

Ser Val Lys Leu Ser Cys Thr Ala Ser Gly Phe Asn Ile Thr Asp Tyr
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asp Thr Glu Tyr Ala Gln Lys Phe
    50                  55                  60

Lys Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Phe Tyr Gly Asp Ala Leu Asp Tyr Trp Gly Gln Gly Thr Thr Val
                100                 105                 110

Thr Val Ser Ser
        115

<210> SEQ ID NO 31
<211> LENGTH: 16
<212> TYPE: PRT
<213> ORGANISM: Artificial Sequence
<220> FEATURE:
<223> OTHER INFORMATION: SYNTHETIC PEPTIDE

<400> SEQUENCE: 31

Lys Ser Ser Gln Ser Leu Leu Asp Ser Asp Gly Lys Thr Tyr Leu Asn
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: SYNTHETIC PEPTIDE

<400> SEQUENCE: 32

Leu Val Ser Lys Leu Asp Ser
1               5
```

```
<210> SEQ ID NO 33
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 33

Trp Gln Gly Thr His Ser Pro Leu Thr
1               5

<210> SEQ ID NO 34
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 34

Thr Ala Ser Gly Phe Asn Ile Thr Asp Tyr Tyr Met His
1               5                   10

<210> SEQ ID NO 35
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 35

Trp Ile Asp Pro Glu Asn Gly Asp Thr Glu Tyr Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: SYNTHETIC PEPTIDE

<400> SEQUENCE: 36

Tyr Gly Asp Ala Leu Asp Tyr
1               5
```